United States Patent [19]
Mierendorf et al.

[11] Patent Number: 5,629,179
[45] Date of Patent: May 13, 1997

[54] METHOD AND KIT FOR MAKING CDNA LIBRARY

[75] Inventors: Robert C. Mierendorf; Barbara B. Morris, both of Madison, Wis.

[73] Assignee: Novagen, Inc., Madison, Wis.

[21] Appl. No.: 406,089

[22] Filed: Mar. 17, 1995

[51] Int. Cl.$^6$ .......................... C12P 19/34; C07H 21/04
[52] U.S. Cl. .................. 435/91.2; 435/91.51; 536/24.33
[58] Field of Search ................... 435/91.1, 91.2, 435/91.51; 536/23.1, 24.2, 24.33

[56] References Cited

U.S. PATENT DOCUMENTS 5,075,227  12/1991  Hagen ................................ 435/91.41

OTHER PUBLICATIONS

Meissner, et al., "Bacteriophage λ cloning system for the construction of directional cDNA libraries," *Proc. Natl. Acad. Sci. USA* 84:4171–4175 (1987).

Palazzolo et al., "A family of lambda phage cDNA cloning vectors, λSWAJ, allowing the amplification of RNA seqences, " *Gene* 32:197–206 (1987).

Palazzolo, et al., "Phage lambda cDNA cloning vectors for subtractive hybridization, fusion–protein synthesis and Cre––loxP automatic plasmid subcloning," *Gene* 88:25–36 (1990).

*Primary Examiner*—George C. Elliott
*Assistant Examiner*—Thanda Wai
*Attorney, Agent, or Firm*—Quarles & Brady

[57] ABSTRACT

A method for forming directionally clonable randomly primed cDNA molecules includes the step of priming first strand synthesis using a set of first strand cDNA primers having the sequence 5'-XXNNNNNN-3' where XX is a constant dinucleotide pair across the set and NNNNNN is a random hexanucleotide, the set including primers representing all random hexanucleotides.

6 Claims, 2 Drawing Sheets

FIGURE 2

```
5'-CGUGCUGCUAAUGGCUGCACGAAAAAAAAA-3'  (mRNA)
3'-GCACGACGATTACCGACGT               (1st strand)
                      T
                     T-5'
```

FIGURE 3

```
5'-CGTGCTGCTAATGGCTGCAAA-3'     (2nd strand)
3'-GCACGACGATTACCGACGTTT-5'     (1st strand)
```

FIGURE 4

```
5'-gcttgaattcaagcCGTGCTGCTAATGGCTGCAAAgcttgaattcaagc-3'
3'-cgaacttaagttcgGCACGACGATTACCGACGTTTcgaacttaagttcg-5'
```

FIGURE 5

```
5'-aattcaagcCGTGCTGCTAATGGCTGCAA-3'       (mRNA synon.)
        3'-gttcgGCACGACGATTACCGACGTTTcga-5'  (template)

EcoRI                           HindIII
```

Italics = primer binding site
DblUnd = random directional primer
Bold = EcoRI site
Und = HindIII site

METHOD AND KIT FOR MAKING CDNA LIBRARY

FIELD OF THE INVENTION

The present invention relates generally to the field of molecular biology and in particular to the creation of gene libraries containing cloned fragments of cDNAs that encode expressed genes.

BACKGROUND OF THE INVENTION

A common practice in molecular biology is to create "gene libraries," which are collections of cloned fragments of DNA that represent genetic information in an organism, tissue or cell type. To construct a library, desired DNA fragments are prepared and inserted by molecular techniques into self-replicating units generally called cloning vectors. Each DNA fragment is therefore represented as part of an individual molecule, which can be reproduced in a single bacterial colony or bacteriophage plaque. Individual clones of interest can be identified by various screening methods, and then grown and purified in large quantities to allow study of gene organization, structure and function.

Only a small fraction of the genetic information for an organism is actually used in an individual cell or tissue at a particular time. A cDNA library is a type of gene library in which only DNA for actively expressed genes is cloned. These active genes can be selectively cloned over silent genes because the DNA for active genes is transcribed into messenger RNA (mRNA) as part of the pathway by which proteins are made. RNA molecules are polar in nature, i.e. the constituent nucleoside bases are linked via phosphodiester bonds between the 3' ribosyl position of one nucleoside and the 5' ribosyl position on the following nucleoside. RNA is synthesized in the 5'→3' direction, and mRNAs are read by ribosomes in the same direction, such that proteins are synthesized from N-terminus to C-terminus. Over the past decade, cDNA libraries have become the standard source from which thousands of genes have been isolated for further study.

The first step in preparing a cDNA library is to purify the mRNA, which usually represents only about 1–3% of the total RNA of the cell, the remainder being ribosomal RNA, transfer RNA, and several other RNA species. Many mRNAs from eukaryotic organisms have a poly(A) "tail," a tract of 50–150 adenosine residues at their 3' ends. A general practice for purifying mRNA from total cellular RNA involves specifically annealing, or binding, the poly(A) tail to oligo(dT), a single stranded DNA molecule of between about 12 and 30 consecutive dT residues (Jacobson, A. (1987) Meth. Enzymol. 152, 254). Total cellular RNA can be incubated with a matrix to which oligo(dT) has been immobilized. Only RNA molecules containing poly(A) tails selectively anneal to the matrix.

Upon purification of poly(A)$^+$ RNA, a double-stranded complementary DNA (cDNA) copy of this active RNA can be synthesized in vitro by two sequential enzymatic steps. An RNA-dependent DNA polymerase, known as a reverse transcriptase, is used to synthesize the first strand cDNA (complementary DNA), using the RNA as a template. Then, a DNA-dependent DNA polymerase, typically *E. coli* DNA polymerase I, copies the newly synthesized first cDNA strand to form a complementary second cDNA strand. A popular method of second strand synthesis utilizes the enzyme RNase H to create "nicks" in the mRNA strand. The resulting short mRNA fragments serve as primers for second strand synthesis by the DNA polymerase (Gubler, U. (1987) Meth. Enzymol. 152, 330). Both polymerases synthesize DNA in the 5'→3' direction, reading the template strand from the 3'→5' direction.

Double-stranded cDNA thus prepared is inserted into a prepared cloning vector. To efficiently insert the cDNA into a cloning vector, the ends of the insert cDNA and the vector DNA molecules must be prepared such that they are compatible. For example, specialized linkers can be added to the cDNA ends, followed by digestion with the relevant enzyme to create single stranded protrusions that will anneal to corresponding ends in the vector. The insert and vector molecules are ligated together with T4 DNA ligase. The ligated vectors carrying their cDNA molecule inserts are then introduced into *E. coli* and screened. Various approaches have been used to prepare the cDNA ends for vector insertion (Kimmel, A. R. and Berger, S. L. (1987) Meth. Enzymol. 152, 307). Most have used the "linker" or "adapter" method described above. All methods using linkers require an additional step to protect the cDNA from being cleaved at adventitious restriction sites during digestion to create the cohesive ends (Wu, R., Wu, T. and Ray, A. (1987) Meth. Enzymol. 152, 343). This protection is accomplished either by treating the cDNA with on site-specific methylases or by substituting a methylated dCTP analog for unmodified dCTP in the synthesis reactions.

In spite of the success of cDNA libraries as a resource, several technical difficulties have limited their wider application or have necessitated a large amount of effort to obtain complete gene sequences. One difficulty concerns the underrepresentation of the 5' ends of gene sequences obtained from cDNA libraries. As noted, first strand synthesis uses an RNA-dependent DNA polymerase. No DNA polymerase can start cDNA synthesis de novo. DNA polymerases require a short primer as a starting material upon which to add bases to the 3' end of a nascent cDNA first strand. The simplest primer is an oligo(dT) primer that can anneal specifically to the 3' poly(A) tail found in most mRNA molecules. All cDNAs synthesized with an oligo(dT) primer thus start at the 3' end of the mRNA and share a common 3' sequence (i.e. the $d(A_n:T_n)$ tail). The major pitfall of oligo (dT)-primed synthesis is that RNA-dependent DNA polymerases tend to become disengaged from the mRNA template before traversing its entire length. It is thought that this is primarily due to random failure in the elongation process and to specific areas of RNA secondary structure at which the enzyme may pause or stop altogether. In oligo(dT)-primed libraries, the 3' ends of mRNAs are, therefore, statistically more likely to be copied than the sequences closer to the 5' end because reverse transcription always commences from the point at which the primer anneals. The resulting cDNA population is therefore biased toward the 3' ends of RNA strands. As might be expected, the effect is particularly noticeable with long mRNAs and results in few or no complete cDNA clones for certain genes in the library. Good quality oligo(dT)-primed cDNA libraries contain some inserts from 4 to 8 kbp, but even inserts of this length may not cover the 5' end of a desired gene.

In addition, some mRNAs have a poly(A) tail that is too short to anneal to the oligo(dT) primer or have no poly(A) tail at all (Greenberg, *Biochemistry* 15:3516–3522 (1976); Adesnik and Darnell, J. Mol. Biol. 67:397–406 (1982); Houdebine, *FEBS Lett.* 66:110–118 (1976)). Estimates of the percent of non-polyadenylated mRNA in different species ranges from 30% (Milcarek et al., *Cell* 3:1–10 (1974)) to 80% (Miller, *Dev. Biol.* 64:118–129 (1978)) of mRNA. In a comparison of poly(A)$^+$ and poly(A)$^-$ mRNA isolated from mouse brain, Van Ness et al., *Cell* 18:1341–1349

(1979) found that a substantial proportion of non-polyadenylated mRNA contains unique protein-encoding sequences. Therefore, many potentially important genes might be unrepresented in oligo(dT)-primed cDNA libraries.

Both of the above-identified problems can be overcome using an alternate type of cDNA primer known as a random primer to produce so-called "random primed libraries." Rather than being a single species, a random primer is, in actuality, a collection or set of primers of a certain length, usually hexameric, wherein the set includes all possible arrangements of the 4 DNA nucleoside bases over the length of the primer. Thus, a random hexamer is actually a collection of $4^6$, or 4096, different primer sequences each of which is capable of annealing specifically with its complementary sequence in mRNA. Since every possible 6-base long portion of the mRNA has a complement in the set of random hexamer primers, the population of cDNA first strands generated using random primers share neither a common origin on the mRNA nor a common 3' sequence. The bias for 3' ends is not a problem in random primed libraries because the primer mix of all possible hexamers promotes initiation of cDNA synthesis at any point on the mRNA. No portion of the mRNA molecule is better represented than any other in the population of cDNA first strands.

A common practice in the field is to supplement screening of oligo(dT)-primed libraries with random primed libraries to obtain full-length clones. Random-primed libraries have also been used for intentionally cloning cDNA fragments as a means to obtain gene regions encoding DNA binding proteins (Singh et al., *Cell* 52:415 (1988); Vinson et al., *Genes Dev.* 2:801 (1988)). The inability of some mRNAs to be primed with oligo(dT) makes it essential to construct random primed libraries when the mRNA is non-polyadenylated.

A popular modification of the standard oligo(dT) priming strategy takes advantage of the common 3' ends of the resulting cDNA to allow the cloning of cDNA molecules in a defined orientation (directional cloning) (Ausubel, et al. (eds) in Current Protocols in Molecular Biology, John Wiley & Sons (1995) Supplement 29). Directional cDNA cloning has two major benefits. First, it reduces the amount of work required to retrieve a clone of interest when using any detection scheme based on protein or peptide expression, such as antibody screening. Expression of the desired protein or peptide requires not only that the DNA fragment containing the gene of interest be present, but also that the fragment is provided in the proper orientation and in the correct reading frame to direct the synthesis of that protein. In a non-directional library, statistically only 1 clone in 6 will meet this requirement, since there are two possible orientations and three possible reading frames for every clone. In contrast, directionally cloned cDNA libraries eliminate the orientation variable, thereby doubling the likelihood of successfully expressing a protein from a given clone and effectively reducing by a factor of two the number of clones that must be screened. The immediate result is diminished labor costs.

The second, and perhaps more important, advantage of directional cloning arises in connection with the construction of subtractive cDNA libraries. Subtractive cDNA libraries are collections of cDNA clones from genes expressed in one tissue or during one developmental state, but not in another. Subtractive cDNA libraries are used to rapidly identify genes important in development or progression of a disease, even in the absence of prior information about the genes. For example, a subtractive cDNA library can identify genes that are specifically active in cancer cells (Scott et al., *Cell* 34:557–567 (1983); Krady et al., *Mol. Brain Res.* 7:287–297 (1990)).

Whereas many strategies have been used to create subtractive libraries, one of the most successful is based on the use of directionally cloned cDNA libraries as starting material (Palazzolo and Meyerowitz, (1987) Gene 52, 197); Palazzolo et al. (1989) Neuron 3, 527; Palazzolo et al. (1990) Gene 88, 25). In this approach, cDNAs prepared from a first source tissue are directionally inserted immediately downstream of a bacteriophage T7 promoter in the vector. Total library DNA is prepared and transcribed in vitro with T7 RNA polymerase to produce large amounts of RNA that correspond to the original mRNA from the first source tissue. Sequences present in both the source tissue and another tissue are subtracted as follows. The in vitro transcribed RNA prepared from the first source is allowed to hybridize with cDNA prepared from either native mRNA or library RNA from the second source tissue. The complementarity of the cDNA to the RNA makes it possible to remove common sequences as they anneal to each other, allowing the subsequent isolation of unhybridized, presumably tissue-specific, cDNA. This approach is only possible using directional cDNA libraries, since any cDNA sequence in a non-directional library is as likely to be in the "sense" orientation as the "antisense" direction (sense and antisense are complementary to each other). A cDNA sequence unique to a tissue would be completely removed during the hybridization procedure if both sense and antisense copies were present.

In one directional cloning strategy, a DNA sequence encoding a specific restriction endonuclease recognition site (usually 6–10 bases) is provided at the 5' end of the oligo(dT) primer (Palazzolo and Meyerowitz 1987). This relatively short recognition sequence does not affect the annealing of the 12–20 base oligo(dT) primer to the mRNA, so the cDNA second strand synthesized from the first strand template includes the new recognition site added to the original 3' end of the coding sequence. After second strand cDNA synthesis, a blunt ended linker molecule containing a second restriction site (or a partially double stranded linker adapter containing a protruding end compatible with a second restriction site) is ligated to both ends of the cDNA. The site encoded by the linker is now on both ends of the cDNA molecule, but only the 3' end of the cDNA has the site introduced by the modified primer. Following the linker ligation step, the product is digested with both restriction enzymes (or, if a partially double stranded linker adapter was ligated onto the cDNA, with only the enzyme that recognizes the modified primer sequence). A population of cDNA molecules results which all have one defined sequence on their 5' end and a different defined sequence on their 3' end.

A related directional cloning strategy developed by Meissner et al. ((1987) Proc. Natl. Acad. Sci USA 84, 4171), requires no sequence-specific modified primer. Meissner et al. describe a double stranded palindromic BamHI/HindIII directional linker having the sequence d(GCTTGGATCCAAGC) (SEQ: ID NO:1), which is ligated to a population of oligo(dT)-primed cDNAs, followed by digestion of the ligation products with BamHI and HindIII. This palindromic linker, when annealed to double stranded form, includes an internal BamHI site (GGATCC) flanked by 4 of the 6 bases that define a HindIII site (AAGCTT). The missing bases needed to complete a HindIII site are d(AA) on the 5' end or d(TT) on the 3' end. Regardless of the sequence to which this directional linker ligates, the internal BamHI site will be present. However, HindIII can only cut the linker if it ligates next to an d(AA):d(TT) dinucleotide base pair. In an oligo(dT)-primed strategy, a HindIII site is always generated at the 3' end of the cDNA after ligation to this directional linker. For cDNAs having the sequence d(TT) at their 5' ends (statistically 1 in 16 molecules), linker addition will also yield a HindIII site at the 5' end. However, because the 5' ends of cDNA are heterogeneous due to the lack of processivity of reverse transcriptases, cDNA products from every gene segment will be represented in the library.

As described above, a major limitation on cDNA cloning technology is imposed by the available priming strategies. Oligo(dT)-primed libraries require poly(A)$^+$ RNA and generally are deficient in 5' sequences. Random primed cDNA libraries have not found general application, partly due to technical difficulties in their construction, and more recently due to the increasing use of incompatible directional cloning strategies. An ideal strategy would combine the directionality of oligo(dT) priming with the sequence independence of random priming. Despite the identified advantages of both random priming and directional cloning, no operative method exists for forming cDNA libraries by directionally cloning random primed cDNAs.

Others have tried, with limited success, to combine random priming and directional cloning. A "5' stretch" technique used in some laboratories employs both an oligo(dT) primer and random hexamers for priming two separate first strand cDNA reactions. The discontinuous cDNA fragments are spliced together during second strand synthesis when the two reactions are combined. After second strand synthesis, linkers of the type described above are added, to facilitate directional cloning. The shortcoming of this strategy is that any spliced cDNA molecule that fails to incorporate oligo (dT) at its 3' end is lost from the library because it cannot regenerate the 3' enzyme recognition sequence that must be present to generate a proper end for ligation. This strategy also does not address the inherent problems attributable to the secondary structure of RNA or to the lack of an adequate poly(A) tail.

Still others have attempted to use a set of random hexameric primers engineered to also include a common restriction site of six or more bases at one end of each primer. These primers have not been successfully used to prime first strand synthesis. The failure has been attributed to the formation of unstable RNA-primer hybrids. Because the length of the engineered restriction site equals or exceeds the length of the random hexamers, proper hybridization of the random portion of the primers may be energetically unfavorable. Moreover, the presence of six defined bases as part of every primer might bias hybridization toward corresponding complementary portions of the RNA templates.

SUMMARY OF THE INVENTION

The present invention provides a method for forming cDNA libraries by directional cloning of cDNA molecules formed by random priming. The method of the present invention differs from existing methods for random priming and directional cDNA cloning in that a novel set of primers having the sequence of 5'-XXNNNNNN-3' is annealed to the RNA templates. The members of the set of primers are constant in one regard and variable in a second regard. The primers in the set vary in the 3'-most six nucleotides, depicted as NNNNNN. This representation is intended to indicate that A, G, C, or T can appear at any position. Thus, the 3'-most six nucleotides of the primers in the set represent all 4096 ($4^6$) possible hexamers.

All primers in the set contain the same two 5'-most nucleotides, depicted as XX. XX can be any dinucleotide that, when ligated to the 3' terminus of another polynucleotide molecule, forms an endonuclease recognition sequence. The use of a dinucleotide is herein demonstrated to be sterically and energetically acceptable to allow primer binding, yet short enough to not bias priming toward any particular sequence on the mRNA templates.

FIG. 1 shows a diagram of the following reactions using the example of EcoRI and HindIII restriction sites, using both oligo(dT) and the directional random primer herein described. The linker DNA containing both the EcoRI and HindIII restriction sites shown as the top strand to the left of the cDNA is identified as SEQ ID NO:2; the linker DNA containing only the EcoRI restriction site shown as the lower strand to the right of the cDNA is represented by bases 3–16 of SEQ ID NO:2.

After binding the set of primers to the RNA strand, first and second strand cDNA syntheses are carried out according to known methods. During copying of the first strand to form the complementary second strand, however, the primer-derived 5'-terminal dinucleotide on the first strand is also copied. Thus, the result of cDNA first and second strand synthesis is a population of fully double-stranded cDNA molecules, each having the same defined dinucleotide at the end corresponding to the 3' (carboxyl-terminal) side of a coding region.

The double-stranded cDNA molecules are joined by ligation to a double-stranded palindromic linker. Internal to the linker is a palindromic second endonuclease recognition sequence different from the first recognition sequence. At the 3' terminus of each strand of the palindromic linker are at least two nucleotides that form the 5' portion of the first endonuclease recognition sequence, the 3' portion of which is encoded by the dinucleotide that is the constant portion shared by each of the primers in the set. Upon ligation of the mixed population of cDNA molecules to copies of the palindromic linker, the second recognition sequence is formed at the junction in each cDNA molecule.

To obtain a cDNA fragment for directional cloning, the ligated products are cleaved using the first and second endonucleases, thereby generating a first cleavage in the linker 5' to the cDNA and a second cleavage at the 3' end of the cDNA in the site formed at the cDNA-linker junction. As normally practiced, the cDNA can be methylated after synthesis using site-specific enzymes (e.g. EcoRI methylase, AluI methylase, etc.) to protect against digestion at adventitious sites. Alternatively, 5-methyl dCTP can be incorporated during cDNA synthesis to accomplish protection.

The directional cDNA fragment thus generated can be ligated directionally into a vector and subsequently prepared as a cDNA library. Notably, the invention permits, for the first time, the generation of a population of randomly primed directional cDNA clones.

The present invention is further summarized in that a kit comprising all 4096 ($4^6$) different oligonucleotide primers having at their 5' ends an additional dinucleotide selected in the manner described above is advantageously employed in the method described.

It is an object of the present invention to provide a method and kit for obtaining randomly-primed, directionally clonable cDNA fragments for use in preparing a directional cDNA library in which are represented all portions of a gene of interest.

It is an advantage of the present invention that directionally clonable cDNAs may be obtained from RNA sequences far 5' to a poly(A) tail, or from RNA molecules that lack a poly(A) tail or from standard poly(A)$^+$ RNA.

It is a feature of the present invention that by appropriately selecting the 5'-terminal dinucleotide of the primer and the linker sequence it is possible to make advantageous selection of both the internal endonuclease recognition sequence as well as the recognition sequence formed at the cDNA-linker junction.

It is another feature of the present invention that the recognition sequence formed at the junction can be any recognition sequence of 4 or more nucleotides.

Other objects, advantages and features of the present invention will become apparent upon consideration of the following detailed description when read in conjunction with the accompanying drawings.

BRIEF DESCRIPTION OF THE DRAWINGS

FIG. 2 illustrates a hypothetical mRNA hybridized to a random directional primer and the first cDNA strand product.

FIG. 3 depicts the double-stranded cDNA formed after synthesis of the second strand and displacement of RNA ribonucleotides of FIG. 2.

FIG. 4 diagrams the cDNA of FIG. 3 linked to 14 base pair long palindromic linkers.

FIG. 5 illustrates the DNA of FIG. 4 following digestion with restriction enzymes.

DETAILED DESCRIPTION OF THE INVENTION

Figure 1:
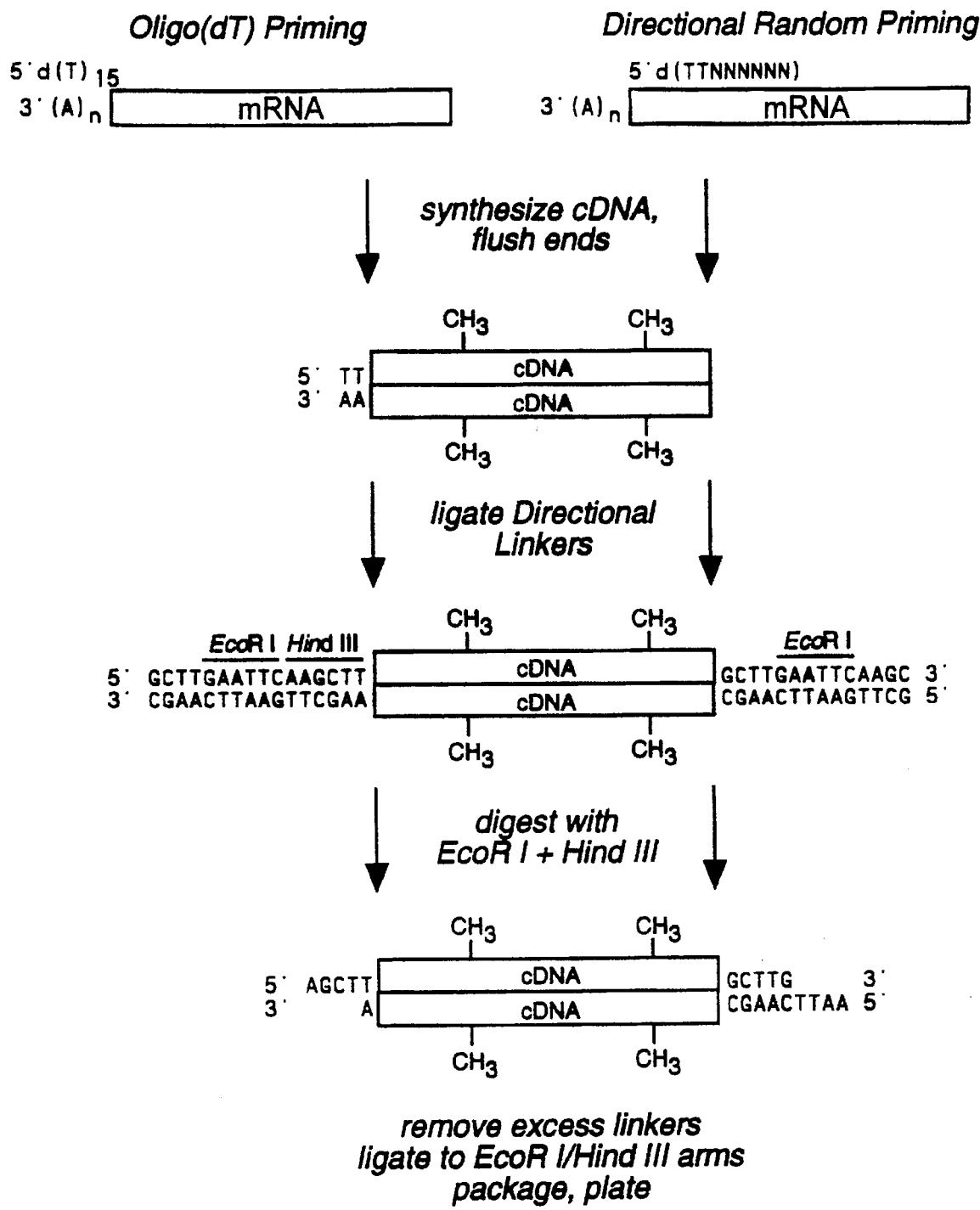
FIG. 1 diagrams steps in the process of the present invention.

The present invention provides a method for forming cDNA libraries by directional cloning of cDNA molecules formed by random priming.

In this application, unless otherwise noted, a reference to a 5' end or a 3' end of a double stranded cDNA molecule is intended to refer to the end of the molecule corresponding to the 5' end or 3' end of the mRNA synonymous strand. The mRNA synonymous strand is the second strand synthesized during cDNA synthesis.

Cellular RNA is isolated using known methods. A preferred method is that of Chomczynski and Sacchi, Anal. Biochem. 162:156–159 (1987). The RNA can be from any organism. The RNA can, but need not be, poly(A)-enriched (poly(A)$^+$). If poly(A)$^+$ RNA is desired, it may be obtained using any method that yields poly(A)-selected RNA. A preferred method for purifying poly(A)-selected RNA is to pass the total RNA over an oligo(dT)-cellulose matrix, washing unbound RNA from the matrix, and then releasing the poly(A)$^+$ RNA from the oligo(dT)-cellulose under low ionic strength with low salt. More recently developed methods for direct isolation of poly(A)+ RNA from tissues and cells utilizing oligo(dT)-coupled magnetic particles may also be employed.

In the method of the present invention, first strand cDNA synthesis begins by mixing the RNA or poly(A)$^+$ RNA with a suitable molar quantity of directional random primers prepared as described herein. The primers can be prepared using standard oligonucleotide synthetic techniques.

The primers, sometimes referred to hereinafter as directional random primers, are a set of 8-mers having the nucleotide sequence 5'-d(XXNNNNNN)-3', each X and each N being a deoxyribonucleotide selected independently from the group consisting of A, G, C, and T, every oligonucleotide comprising an identical 5' terminal dinucleotide portion XX selected from the group consisting of AA, AG, AC, AT, CA, CG, CC, CT, GA, GG, GC, GT, TA, TG, TC, and TT, each 8-mer further comprising a single random hexanucleotide portion NNNNNN, the set of primers comprising every 8-mer having the noted constant XX and variable NNNNNN sequences.

The set of directional random primers are mixed with the total RNA or poly(A)$^+$ RNA and processed under suitable conditions to promote first strand cDNA synthesis. Initially, the mixture of primers and RNA is, for a sufficient time, brought to a temperature sufficiently high to denature double-stranded portions of the nucleic acids. A denaturing step at 70° C. for 10 minutes is suitable. While reaction components are added, the mixture is kept chilled to prevent renaturation or priming. Reaction components are added to bring the mixture to a suitable buffered pH and ionic strength, to allow RNA-dependent DNA synthesis to proceed. Also added to the reaction are deoxynucleotide triphosphates for incorporation into the first cDNA strand and an RNA-dependent DNA polymerase such as a retroviral reverse transcriptase. A preferred reverse transcriptase is the Moloney murine leukemia virus reverse transcriptase.

If desired, dCTP can be replaced in the reaction mix with 5-methyl dCTP. Incorporation of 5-methyl dCTP into the growing first strand protects the synthetic DNA from cleavage by restriction endonucleases. It is desirable to avoid internal cleavage of cDNAs formed by the method so that the only restriction endonuclease recognition sequences used are those provided in the method.

When the first strand synthesis reaction components have been added, the mixture is incubated for a sufficient time and at a temperature appropriate for RNA-dependent DNA polymerization. Incubation at 37° C. for 60 minutes is suitable. When first strand synthesis is complete, the reaction is heated to a sufficiently high temperature for an adequate length of time to inactivate the RNA-dependent DNA polymerase (e.g., 70° C. for 10 minutes).

The products of cDNA first strand synthesis are single stranded DNAs. The specific sequence close to the 5' end of any one such strand depends upon which primer initiated the strand. Since all 4096 possible hexamers are represented among the primers, a cDNA molecule is initiated at a position complementary to each position on the RNA template molecules. At the 5' terminus of each first strand, however, is a dinucleotide that need not be complementary to the corresponding nucleotides in the RNA template. At some frequency, however, there will be a 7, or even 8, base complementarity between the RNA and the 8-mer. One hypothetical first strand and its complementary RNA template are shown schematically in FIG. 2. The hypothetical first strand is also presented as SEQ ID NO:91. The complementary cDNA first strand is set forth in SEQ ID NO:92. It is noted that the mRNA depicted in FIG. 2 is not intended to show a full length RNA molecule; rather, a short molecule is indicated for illustrative purposes only. Shown in italics in the mRNA of FIG. 2 is a 6 base long primer binding site. The primer binding site shown is not, though could be, in the poly(A) tail of an mRNA. FIG. 2 also depicts, in double underline, an example of the 8 base long random directional primer of the present invention. Six of the 8 bases are bound to the primer binding site of the mRNA. The 5' terminal dinucleotide, however, remains unbound during first strand synthesis. FIG. 2 also depicts the first strand product of the reverse transcription reaction described above. It is to be understood, of course, that this depiction in FIG. 2 represents only a single priming event and that other primers are similarly priming at every other 6 base long stretch of each RNA molecule in the reaction mixture.

Second strand cDNA synthesis can proceed in the same reaction vessel as the first strand synthesis reaction. The reaction mixture is adjusted to buffering conditions appropriate for DNA polymerization using a DNA-dependent DNA polymerase. A preferred DNA polymerase is *E. coli* DNA polymerase I and an appropriate polymerization buffer for DNA polymerase I is set forth in the examples below. Also added to the second strand synthesis reaction are nucleotides for incorporation into a nascent second strand. As was the case in first strand synthesis, dCTP can, if desired, be replaced with 5-methyl dCTP so that the second strand will also be methylated, and thereby protected from cleavage by restriction endonucleases. Hemi-methylated and fully-methylated DNA are protected from cleavage by most restriction endonucleases. Another acceptable method for protecting against digestion at internal sequences is to treat the cDNA fragments with a specific DNA methylase prior to linker ligation. Finally, an agent for introducing nicks into the RNA strand is added to the second strand reaction. By introducing nicks into the RNA strand, the DNA-dependent DNA polymerase can utilize the nicked RNA strands as primers for second strand DNA synthesis. During second strand synthesis, remaining RNA residues are displaced from the first strand by the growing second strand. A suitable nicking agent is RNase H (Okayama, H. and Berg, P. (1982) Mol. Cell. Biol. 2, 161; Gubler, U. and Hoffman, B. (1983) Gene 25, 263). When the reaction components have been added, the second strand synthesis reaction is allowed to proceed for a suitable length of time at a temperature adequate to support DNA-dependent DNA polymerization. A suitable incubation condition is 15° C. for 90 minutes. When second strand synthesis is complete, the double-stranded cDNA molecules thus formed are purified from the reaction components. Proteins can be inactivated and removed from the mixture by phenol:chloroform:isoamyl alcohol extraction. The double stranded cDNA is then precipitated with alcohol, centrifuged, and resuspended in water. FIG. 3 depicts schematically the cDNA molecule formed after second strand priming and synthesis and displacement of remaining ribonucleotides. SEQ ID NO:93 sets forth the second strand (upper strand in FIG. 3) generated complementary to the first strand of SEQ ID NO:92.

Following second strand synthesis 3' single stranded protrusions or overhangs commonly remain on the cDNA due to dissociation of short primers near the termini. Therefore, it is desirable to remove any overhanging bases in the cDNA molecules thus formed. An appropriate enzyme for "trimming" 3' extensions and/or adding terminal nucleotides to fill in 5' overhang ends is T4 DNA polymerase. Conditions for making double stranded DNA blunt ended are well known, and exemplary conditions including buffers and nucleotides are set forth in the examples below.

The next step in the method is to ligate the ends of the cDNA molecule to a pair of palindromic linkers, the sequence of which is selected to meet the requirements set forth below. First, the palindromic linker includes an internal palindromic recognition endonuclease sequence. Many such palindromic sequences are known. It is preferred that the internal palindromic sequence be 6 or more nucleotide pairs in length. Palindromic restriction endonuclease sequences up to 8 base pairs are commonly used in cloning. The second requirement of the palindromic linker is that it contain, at the 5' end of each strand, a portion of an endonuclease recognition sequence that, when ligated to the 3' end of the mRNA synonymous cDNA second strand, will form a desired endonuclease recognition sequence, the existence of which depends entirely upon the introduction of the random directional primer during first strand cDNA synthesis. This aspect of the invention is depicted in FIG. 4 where the cDNA of FIG. 3 is shown with 14 base pair long palindromic linkers, shown in lower case, attached to both ends of the cDNA molecule of FIG. 3. The full length top strand in FIG. 4 is set forth as SEQ ID NO:94. Note that, as in FIG. 3, the primer-derived portion of the cDNA molecule is double underlined. Also, internal palindromic restriction sites, in this case 5'-gaattc-3', are shown in bold in each linker. At the junction between the 3'-end of the cDNA and the linker, a newly-generated endonuclease recognition sequence is shown. In this case, the sequence, 5'-AAgctt-3', encodes a Hind III recognition sequence. Finally, note that at the opposite end of the cDNA molecule, no comparable Hind III site is formed. It is, of course, possible that an endonuclease recognition sequence could be formed at the opposite end of the molecule, if the 2 5'-terminal bases of the mRNA synonymous strand happened to match those at the 3' end of the same strand. Statistically, this occurs in 1 of 16 molecules. Given the random nature of the priming step, this is of no concern, since all portions of the gene of interest are redundant in the library.

The selection of a linker Sequence depends entirely upon the 2 endonucleases one desires to use in directionally cloning the cDNA products. In theory, there are no size constraints placed upon the linker, although certain G-C rich oligonucleotides may be impractical due to their propensity to form "hairpin" self-annealed structures rather than duplexes. Additional restriction sites may be included in longer linkers. As noted above, the internal recognition sequence of the linker can be any palindromic sequence of any length, preferably equal to or greater than 6 base pairs. Table 1 presents a representative listing of some possible combinations of primer XX portions and linker end sequences along with the names of available restriction endonucleases that cleave sites generated by particular combinations. To illustrate this, the first row of the table demonstrates that when the XX portion of the directional random primer is AA and the linker is AATTAAXXXXXXTTAATT (SEQ: ID NO:5), a PacI site is created upon ligation. Bases separated by a slash in Table 1 can be either base of the pair surrounding the slash where the appropriate complementarity is maintained between the 5' end and the 3' end of the linker strands. Likewise, where the table indicates Py for pyrimidine or Pu for purine, appropriate complementarity must also be maintained. Note that Xs are used to denote internal restriction sequences of unspecified length. These internal Xs are not the same as the terminal XX portions of the sets of primers. Nucleotides N are intended to represent positions wherein the particular nucleotide sequence is irrelevant to cleavage with the noted restriction enzymes.

Note also that 37 C.F.R. §1.821(a) specifies that the directional linkers of Table 1 shall be included in the accompanying Sequence Listing. However, the limitation of the nucleotide codes available to specify an undefined nucleotide in the Sequence Listing make it impossible to distinguish nucleotides N from nucleotides X as shown in Table 1. In addition, one cannot distinguish in the Sequence Listing among complementary nucleotides when either is acceptable as long as complements exist at a pair of positions. Thus, certain information specified in Table 1 is missing from the Sequence Listing. While the Sequence Listing is accurate within the limits of the IUPAC coding system, Table 1 is a more useful source of information concerning embodiments of the invention.

TABLE I

Restriction sites created by defined dinucleotide ends of directional random primers

| Directional random primer (5'-3') | Directional linker (5'-3') | | Restriction site(s) after ligation |
|---|---|---|---|
| AANNNNNN | CGAAXXXXXXTTCG | SEQ:ID:NO: 3 | BstB I |
| | AAXXXXXXXTT | SEQ:ID:NO: 4 | Mxe I |
| | AATTAAXXXXXXTTAATT | SEQ:ID:NO: 5 | Pac I |
| ACNNNNNN | CGACXXXXXXGTCG | SEQ:ID:NO: 6 | Sal I, Acc I |
| | GTGCXXXXXXGCAC | SEQ:ID:NO: 7 | ApaL I |
| | GCACXXXXXXGTGC | SEQ:ID:NO: 8 | BsiHKA I, Bsp1286 I |
| | ACXXXXXXGT | SEQ:ID:NO: 9 | Csp6 I |
| AGNNNNNN | TAAGXXXXXXCTTA | SEQ:ID:NO: 10 | Afl II |
| | CGAGXXXXXXCTCG | SEQ:ID:NO: 11 | Ava I, Xho I |
| | AGXXXXXXCT | SEQ:ID:NO: 12 | Bfa I |
| | GCAGXXXXXXCTGC | SEQ:ID:NO: 13 | Pst I, Sfc I |
| ATNNNNNN | TAATXXXXXXATTA | SEQ:ID:NO: 14 | Ase I |
| | CGATXXXXXXATCG | SEQ:ID:NO: 15 | Cla I |
| | GCATXXXXXXATGC | SEQ:ID:NO: 16 | Nsi I, Ppu10 I |
| CANNNNNN | ATCAXXXXXXTGAT | SEQ:ID:NO: 17 | Bcl I |
| | TACAXXXXXXTGTA | SEQ:ID:NO: 18 | BsrG I |
| | GCCAXXXXXXTGGC | SEQ:ID:NO: 19 | Eae I |
| CCNNNNNN | GCCCXXXXXXGGGC | SEQ:ID:NO: 20 | Apa I, Ban II, Bsp120 I |
| | CGCGCCXXXXXXGGCGCG | SEQ:ID:NO: 21 | Asc I |
| | T/ACCXXXXXXGGA/T | SEQ:ID:NO: 22 | Ava II |
| | ATCCXXXXXXGGAT | SEQ:ID:NO: 23 | BamH I, BstY I |
| | PyPuCCXXXXXXGGPyPu | SEQ:ID:NO: 24 | Ban I |
| | CGCCXXXXXXGGCG | SEQ:ID:NO: 25 | BsaH I, Hae II, Kas I, Nar I |
| | TNACCXXXXXXGGTNA | SEQ:ID:NO: 26 | BstE II |
| | GNCCPyXXXXXXPuGGNC | SEQ:ID:NO: 27 | Eco0109 I, PpuM I (N = A/T) |
| | TACCXXXXXXGGTA | SEQ:ID:NO: 28 | Kpn I, Asp718 I, Acc65 I |
| | NCCXXXXXXGGN | SEQ:ID:NO: 29 | Sau96 I |
| | CCNNNNNNGGCCXXXXXXGGCCNNNNNNGG | SEQ:ID:NO: 30 | Sfi I |
| CGNNNNNN | CGCGXXXXXXCGCG | SEQ:ID:NO: 31 | Ava I, BsiE I |
| | TACGXXXXXXCGTA | SEQ:ID:NO: 32 | BsiW I |
| | GCCGXXXXXXCGGC | SEQ:ID:NO: 33 | Eae I, Eag I |
| | ATCGXXXXXXCGAT | SEQ:ID:NO: 34 | Pvu I |
| | GA/TCCGXXXXXXCGGA/TC | SEQ:ID:NO: 35 | Rsr II |
| | CCGGCGXXXXXXCGCCGG | SEQ:ID:NO: 36 | SrgA I |
| CTNNNNNN | ATCTXXXXXXAGAT | SEQ:ID:NO: 37 | Bgl II, BstY I |
| | GNCCTXXXXXXAGGNC | SEQ:ID:NO: 38 | Eco0109 I, PpuM I (N = A/T) |
| | CGCTXXXXXXAGCG | SEQ:ID:NO: 39 | Hae II |
| GANNNNNN | CGGAXXXXXXTCCG | SEQ:ID:NO: 40 | BsaW I, BspE I |
| | ATGAXXXXXXTCAT | SEQ:ID:NO: 41 | BspH I |
| | GAXXXXXXTC | SEQ:ID:NO: 42 | Taq I |
| | TAGAXXXXXXTCTA | SEQ:ID:NO: 43 | Xba I |
| GCNNNNNN | CNNNNNGGCXXXXXXGCCNNNNNG | SEQ:ID:NO: 44 | Bgl I |
| | TNAGCXXXXXXGCTNA | SEQ:ID:NO: 45 | Epu1102 I |
| | CGGCXXXXXXGCCG | SEQ:ID:NO: 46 | BsrF I, NgoM I |
| | GCGCXXXXXXGCGC | SEQ:ID:NO: 47 | BssH II |
| | NGCXXXXXXGCN | SEQ:ID:NO: 48 | Fnu4H I |
| | GCXXXXXXGC | SEQ:ID:NO: 49 | Hha I, HinP1 I |
| | NNNNNNGCXXXXXXGCNNNNNN | SEQ:ID:NO: 50 | Mwo I |
| | TAGCXXXXXXGCTA | SEQ:ID:NO: 51 | Nhe I |
| | GGCCGCXXXXXXGCGGCC | SEQ:ID:NO: 52 | Not I |
| | ATGCXXXXXXGCAT | SEQ:ID:NO: 53 | Sph I, Nsp I |
| GGNNNNNN | CGGGXXXXXXCCCG | SEQ:ID:NO: 54 | Ava I, BsaJ I, Xma I |
| | TAGGXXXXXXCCTA | SEQ:ID:NO: 55 | Avr II |
| | NNNNNNGGXXXXXXCCNNNNNN | SEQ:ID:NO: 56 | Bsl I |
| | A/TGGXXXXXXCCA/T | SEQ:ID:NO: 57 | BstN I |
| | ANNNNNNTGGXXXXXXCCANNNNNNT | SEQ:ID:NO: 58 | BstX I |
| | TNAGGXXXXXXCCTNA | SEQ:ID:NO: 59 | Bsu36 I |
| | TNNNNNAGGXXXXXXCCTNNNNNA | SEQ:ID:NO: 60 | EcoN I |
| | GGXXXXXXCC | SEQ:ID:NO: 61 | Hpa II, Msp I |
| | GCGGXXXXXXCCGC | SEQ:ID:NO: 62 | MspA1 I, Sac II, Dsa I |
| | C/GGGXXXXXXCCC/G | SEQ:ID:NO: 63 | Nci I, ScrF I |
| | ATGGXXXXXXCCAT | SEQ:ID:NO: 64 | Nco I, Sty I |
| | ANNNNNTGGXXXXXXCCANNNNNT | SEQ:ID:NO: 65 | PflM I |
| | ANNNNNNNNGGTXXXXXXCCANNNNNNNNT | SEQ:ID:NO: 66 | Xcm I |
| | TGCAGGXXXXXXCCTGCA | SEQ:ID:NO: 67 | Sse8387 I |
| GTNNNNNN | PuPyGTXXXXXXACPuPy | SEQ:ID:NO: 68 | Afl III |
| | CGGTXXXXXXACCG | SEQ:ID:NO: 69 | Age I, BsaW I, BsrF I |
| | GCGTXXXXXXACGC | SEQ:ID:NO: 70 | Mlu I |
| | TAGTXXXXXXACTA | SEQ:ID:NO: 71 | Spe I |
| TCNNNNNN | CGTCXXXXXXGACG | SEQ:ID:NO: 72 | Aat II, BsaH I |
| | ATTCXXXXXXGAAT | SEQ:ID:NO: 73 | Apo I, EcoR I |
| | GCTCXXXXXXGAGC | SEQ:ID:NO: 74 | Ban II, Sac I, BsiHKA I, Bsp1286 I |
| | TCXXXXXXGA | SEQ:ID:NO: 75 | Dpn II, Mbo I, Sau3A I |

TABLE I-continued

Restriction sites created by defined dinucleotide ends of directional random primers

| Directional random primer (5'-3') | Directional linker (5'-3') | | Restriction site(s) after ligation |
|---|---|---|---|
| | CNNNNNNGTCXXXXXXGACNNNNNNG | SEQ:ID:NO: 76 | Drd I |
| | CNNNNNGTCXXXXXXGACNNNNNG | SEQ:ID:NO: 77 | Eam1105 I |
| | NTCXXXXXXGAN | SEQ:ID:NO: 78 | Hinf I, Tfi I (N = A/T) |
| | CNNNGTCXXXXXXGACNNNG | SEQ:ID:NO: 79 | Tth111 I |
| TGNNNNNN | GNNNCTGXXXXXXCAGNNNC | SEQ:ID:NO: 80 | AlwN I |
| | CGTGXXXXXXCACG | SEQ:ID:NO: 81 | Ava I |
| | CNNNGTGXXXXXXCACNNNG | SEQ:ID:NO: 82 | Dra III |
| | ATTGXXXXXXCAAT | SEQ:ID:NO: 83 | Mun I |
| | TATGXXXXXXCATA | SEQ:ID:NO: 84 | Nde I |
| | TGXXXXXXCA | SEQ:ID:NO: 85 | Nla III |
| | CCGGTGXXXXXXCACCGG | SEQ:ID:NO: 86 | SgrA I |
| TTNNNNNN | ATTTXXXXXXAAAT | SEQ:ID:NO: 87 | Apo I |
| | GCTTXXXXXXAAGC | SEQ:ID:NO: 88 | Hind III |
| | TTXXXXXXAA | SEQ:ID:NO: 89 | Tsp509 I |

When a suitable linker sequence has been determined, the linker itself can be synthesized using standard oligonucleotide synthetic techniques. Since the double-stranded linker is palindromic, only a single linker strand need be generated. To convert the single stranded linker into double stranded form, the linker is heated to an appropriate temperature for an adequate length of time to denature and remove any secondary structure from the oligonucleotide and then the oligonucleotide is allowed to cool slowly to room temperature to anneal pairs of the molecules to a fully double stranded form. In most cases heating to 95° C. for 10 minutes before annealing is suitable.

The double stranded linker is then ligated to the blunt ended cDNA molecules under standard ligation conditions. It is necessary to phosphorylate the linkers prior to ligation with cDNA using T4 polynucleotide kinase, if the primers were not phosphorylated chemically during synthesis. Phosphorylation of the linkers ensures that covalent phosphodiester bonds will be formed with both cDNA strands, thereby rendering the ligation products stable to thermal treatments, such as those used to inactivate ligase following the reaction (commonly 70° C., 10 minutes). Ligation is allowed to proceed in linker excess under standard ligation conditions, such as those set forth in the examples below, for a suitable length of time. The ligase is then inactivated. It is preferred that the inactivation be performed by heating the reaction to a temperature sufficiently high to inactivate the enzyme. If the enzyme is heat inactivated, the subsequent restriction digestion can be performed in the same reaction vessel.

Restriction digestion can proceed under well known and established conditions appropriate for the enzymes chosen. Digestion with the two enzymes can be sequential or concurrent if enzyme buffer conditions permit. The outcome of the double digestion is shown schematically in FIG. 5 where the cDNA molecule of the preceding figures is now shown to have, at its 5' end, an introduced EcoRI site, and at its 3' end, an introduced Hind III site. The sequences which make up the double-stranded DNA in FIG. 5 are presented as SEQ ID NO:95 (mRNA synon.) and SEQ ID NO:96 (template). The sequences introduced at the two ends of the cDNA are well defined by the preceding steps and therefore, cannot be mistaken for RNA-derived sequences. After restriction digestion, the cDNA molecules are then prepared for cloning.

To prepare for the cloning, the restriction endonucleases are removed by extraction with phenol, leaving the cDNA molecules in the aqueous phase. Preferably, the cDNAs can be size fractionated to remove very small cDNA molecules and excess linker fragments from the population. A suitable method for size fractionization is size-exclusion chromatography on a column such as a Sepharose CL-4B (Pharmacia, Piscataway, N.J.) column in TE buffer plus 0.3M sodium acetate. Under these conditions, cDNA molecules smaller than about 300 base pairs are included by the column and those larger molecules passing through the column in the void fractions can be pooled, precipitated, and resuspended in water or buffer.

The cDNA molecules thus prepared, are then packaged in a manner known to the art by ligation to the vector DNA (e.g. λ phage DNA arms appropriately digested with endonucleases to match the ends of the cDNA molecules).

Beyond this stage, in vitro packaging/infection, transfection and/or transformation, screening and analysis of cDNA clones can proceed in a standard manner. Exemplary conditions are set forth in the Examples.

The cDNA molecules with appropriately digested ends can also be cloned into phage or plasmid expression vectors which can then be introduced into appropriate host bacteria or other cells that support transcription and translation of the introduced DNA, and screened, using known screening methods for detecting a protein or peptide of interest. As noted above, consideration must be given to the reading frames of clones generated and an appropriate number of expression vector clones must be screened to increase the likelihood that a single desired clone will be obtained. Other vectors and hosts can be used that do not support protein expression, since directional libraries can also be screened using conventional nucleic acid probe techniques.

Thus, it has been demonstrated that by providing a directional random primer in accordance with the present invention, the present inventors have enabled a method that permits, for the first time, the combination of random priming and directional cloning in a single method. As a result, preparation, detection, and production of desired cDNA molecules is more readily accomplished.

Having demonstrated the advantage of the directional random primers of the present invention, it is also desired to provide a kit comprising the set of oligonucleotides having the sequence 5'-XXNNNNNN-3' wherein X and N are as described above. Provision of this kit further facilitates performance of the library preparation in accordance with the present invention. It is noted, of course, that a separate kit would be required for each set of oligonucleotides depending upon the choice of the XX dinucleotide and the linker sequence. As noted, XX can be AA, AG, AC, AT, GA, GC, GG, GT, CA, CG, CC, CT, TA, TG, TC, or TT.

EXAMPLES

1. Directional Random Primer

A desalted, deprotected 8-mer with the sequence 5'-d (TTNNNNNN) was obtained from a commercial custom oligonucleotide source. Lyophilized oligonucleotide was resuspended in TE buffer (10 mM Tris pH 8.0, 1 mM EDTA) to a concentration of 1.0 mg/ml.

2. Preparation of RNA

Total *Drosophila melanogaster* RNA was isolated from 14–16 hour old embryos by the method of Chomczynski and Sacchi, *Anal. Biochem.* 162:156–159 (1987). Poly(A)$^+$ RNA was separated from total RNA by two rounds of purification on oligo(dT)-cellulose (Collaborative Biomedical Products, Bedford, Mass.) according to the manufacturer's protocol.

3. First Strand cDNA Synthesis

Four µg of poly(A)+ RNA and 1 µg of directional random primer were mixed with water in total volume of 20 µl and were heated to 70° C. for 10 minutes. The mixture was chilled on ice and the following components were added: 10 µl of 5× first strand buffer (250 mM Tris-HCl, pH 8.3 at 25° C., 375 mM KCl, 15 mM MgCl$_2$), 5 µl of 100 mM dithiothreitol, 2.5 µl methylation dNTP mix (Novagen, Inc.; 10 mM each dATP, dGTP, dTTP and 5-methyl dCTP), 1000 units of Moloney murine leukemia virus reverse transcriptase (Bethesda Research Labs, Gaithersburg, Md.) and water to a final volume of 50 µl. The reaction mixture was incubated at 37° C. for 60 minutes. The enzyme was inactivated by heating the reaction to 70° C. for 10 minutes.

4. Second Strand cDNA Synthesis

The following components were added directly to the first strand reaction after the heat inactivation step. 50 µl of 5× second strand buffer (200 mM Tris-HCl, pH 7.5, 22 mM MgCl$_2$, 425 mM KCl), 6 µl of 100 mM dithiothreitol, 2 µl of methylation dNTP mix, 50 units of DNA polymerase I (Promega, Madison, Wis.) and 1.6 units RNase H (Promega) in a total volume of 250 µl. The second strand reaction was incubated at 15° C. for 90 minutes. The reaction was terminated by extraction with an equal volume of TE-buffered phenol:chloroform:isoamyl alcohol (25:24:1). The double-stranded cDNA thus formed was precipitated by the addition of 1 volume of 4M ammonium acetate and 0.6 volume of isopropanol, incubation at room temperature for 5 minutes) and centrifugation at 12000×g at room temperature for 8 minutes. The pellet was rinsed with 70% ethanol, air dried and resuspended in 20 µl of nuclease-free water.

5. Blunting Ends of cDNA

The following was added to the resuspended cDNA: 1.5 µl of 1M Tris-HCl, pH 7.5, 1.5 µl of 1 mg/ml acetylated bovine serum albumin, 1.5 µl of 100 mM dithiothreitol, 1.5 µl of 100 mM MgCl$_2$, 3 µl of 1 mM dNTP mix (1 mM each dATP, dGTP, dTTP and dCTP), 5 units of T4 DNA polymerase (Novagen) and nuclease-free water to a final volume of 30 µl. Following incubation at 11° C. for 20 minutes, the blunt ended cDNAs were extracted and precipitated as described above. The final pellet was resuspended in 13 µl of nuclease-free water.

6. Preparation of Linker

The directional EcoRI/HindIII linker with the sequence 5'-d(GCTTGAATTCAAGC) (SEQ: ID NO:90) was obtained from a commercial custom oligonucleotide source. The HPLC-purified oligonucleotide was resuspended in TE buffer at a concentration of 1000 pmol/µl, heated to 95° C. for 10 minutes and allowed to cool slowly to room temperature to anneal pairs of the molecules to a fully double-stranded form.

7. Ligation of cDNA to Linker

Because neither the primers used for cDNA synthesis nor the linkers were chemically phosphorylated during synthesis, the linkers and cDNA were treated together with polynucleotide kinase immediately before use. To the blunt ended cDNA were added 2 µl of 10× ligase buffer (500 mM Tris HCl, pH 8.0, 15 mM MgCl$_2$, 100 mM dithiothreitol, 500 µg/ml of acetylated bovine serum albumin), 2 µl of 1 mM ATP, 100 pmol of directional linkers and 5 units of polynucleotide kinase (Novagen). The reaction was incubated at 37° C. for 5 minutes to allow phosphorylation, then placed on ice. Six Weiss units of T4 DNA ligase (Novagen) were added. The ligation was incubated for 16 hours at 16° C. The ligase was inactivated by heating to 70° C. for 10 minutes.

8. Restriction Digestion of cDNA

The following reagents were added to the ligation reaction: 8 µl of 100 mM Tris-HCl pH 7.5, 8 µl of 10 mM MgCl$_2$, 5 µl of 1M NaCl, 10 µl of 1 mg/ml acetylated BSA, 100 units HindIII (New England Biolabs) and water to a final volume of 100 µl. Following a 2 hour incubation at 37° C., 10 µl of 1M Tris-HCl, pH 7.5 and 100 units of EcoRI (Promega) were added and the incubation was continued for another 4 hours. The enzymes were inactivated by extraction with 1 volume of TE-buffered phenol:chloroform:isoamyl alcohol (25:24:1). The aqueous phase containing the cDNA was used for size fractionation in the next step.

9. Size Fractionation of cDNA cDNA molecules smaller than 300 base pairs in length were removed by size-exclusion chromatography on a 2 ml Sepharose CL-4B (Pharmacia, Piscataway, N.J.) column in TE buffer plus 0.3M sodium acetate. The void fractions containing cDNAs larger than 300 base pairs were pooled and the DNA was precipitated with ethanol and resuspended in 15 µl of water.

10. Ligation and Packaging of cDNA

The following ligation reaction was assembled: 3 µl of size fractionated cDNAs, 0.5 µg of λ SHlox® EcoRI/HindIII-digested vector arms (Novagen), 1 µl of 10× ligase buffer, 1 µl of 10 mM ATP, 0.6 units of T4 DNA ligase in a total volume of 10 µl. The ligation reaction was incubated for 4.5 hours at 16° C. and the entire reaction was packaged in 1 PhageMaker® in vitro packaging extract (Novagen). The titer of the resulting cDNA library was determined by plating serial dilutions of the packaged phage on *E. coli* strain ER1647. A total library of 2.3×10$^6$ primary recombinants was obtained by pooling the packaging reactions resulting from 4 additional ligations performed with the remainder of the size-fractionated cDNAs.

We claim:

1. A method for making a cDNA library, the method comprising the steps of:

annealing a set of primers to a mixed population of template RNA strands under suitable annealing conditions, the set of primers having a sequence of 5'-XXNNNNNN-3', each X end each N being a deoxyribonucleotide selected from the group consisting of A, G, C and T, every primer comprising an identical 5' terminal dinucleotide portion XX selected so as to define a 3' portion of a first endonuclease recognition sequence cleavable by a first endonuclease, each primer further comprising a single random hexanucleotide portion NNNNNN, the set of primers comprising every random hexanucleotide;

reverse transcribing the primed template RNA strands to form a mixed population of cDNA first strands hybridized to the template RNA strands, each cDNA first strand having at its 5' terminus the 5'-XXNNNNNN-3' sequence of a single primer;

adding a DNA dependent DNA polymerase and synthesizing a cDNA second strand complementary to the cDNA first strands, displacing the template RNA strands, and creating a mixed population of fully double-stranded cDNA molecules, each cDNA second strand having at its 3'-terminus a dinucleotide sequence complementary to the selected 5' terminal dinucleotide portion XX of the cDNA first strands;

ligating together under suitable ligation conditions the mixed population of cDNA molecules and a double-stranded palindromic linker that comprises an internal second endonuclease recognition sequence, different from the first recognition sequence and cleavable by a second endonuclease, and a 5' portion of the first endonuclease recognition sequence, the 5' portion comprising at least two complementary nucleotide pairs at each 3' terminus of the palindromic linker, whereupon the second recognition sequence is formed;

cleaving the products of the preceding ligation step using the first endonuclease and the second endonuclease to form a mixed population of directional cDNA fragments each having two ends, the two ends of each fragment being distinct and incompatible with each other;

ligating the population of directional cDNA fragments in a desired orientation into a vector capable of propagating a cDNA library, the vector having been prepared with termini that are ligation-compatible with the ends of the directional cDNA fragments;

introducing the vector-ligated fragments into a bacterial host cell that supports transcription of introduced sequences.

2. A method as claimed in claim 1 wherein the 5' terminal dinucleotide portion of the primers is selected from the group consisting of AA, AG, AC, AT, CA, CG, CC, CT, GA, GG, GC, GT, TA, TG, TC, and TT.

3. A method as claimed in claim 1 wherein the 5' terminal dinucleotide portion of the primers is TT.

4. A method as claimed in claim 1 wherein the second endonuclease recognition sequence is a six base-pair long palindromic sequence.

5. A method as claimed in claim 1 wherein the palindromic linker is between 10 and 32 base pairs in length.

6. A kit, comprising:

single stranded oligonucleotides having a sequence of 5'-XXNNNNNN-3', each X and each N being a deoxyribonucleotide selected from the group consisting of A, G, C and T, every oligonucleotide comprising an identical 5' terminal dinucleotide portion XX selected from the group consisting of AA, AG, AC, AT, CA, CG, CC, CT, GA, GG, GC, GT, TA, TG, TC, and TT, each oligonucleotide further comprising a single random hexanucleotide portion NNNNNN.

* * * * *

SEQUENCE LISTING ( 1 ) GENERAL INFORMATION:

( i i i ) NUMBER OF SEQUENCES: 96

( 2 ) INFORMATION FOR SEQ ID NO:1:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Synthetic DNA Linker"

( x i ) SEQUENCE DESCRIPTION: SEQ ID NO:1:

GCTTGGATCC AAGC                      14

( 2 ) INFORMATION FOR SEQ ID NO:2:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic DNA Linker"

( x i ) SEQUENCE DESCRIPTION: SEQ ID NO:2:

GCTTGAATTC AAGCTT                 16

( 2 ) INFORMATION FOR SEQ ID NO:3:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic DNA Linker"

( i i i ) HYPOTHETICAL: YES ( x i ) SEQUENCE DESCRIPTION: SEQ ID NO:3:

CGAANNNNNN TTCG                     14

( 2 ) INFORMATION FOR SEQ ID NO:4:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic DNA Linker"

( i i i ) HYPOTHETICAL: YES ( x i ) SEQUENCE DESCRIPTION: SEQ ID NO:4:

AANNNNNNTT                         10

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic
            DNA Linker"

( i i i ) HYPOTHETICAL: YES ( x i ) SEQUENCE DESCRIPTION: SEQ ID NO:5:

AATTAANNNN NNTTAATT                                18

( 2 ) INFORMATION FOR SEQ ID NO:6:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic
            DNA Linker"

( i i i ) HYPOTHETICAL: YES ( x i ) SEQUENCE DESCRIPTION: SEQ ID NO:6:

CGACNNNNNN GTCG                                      14

( 2 ) INFORMATION FOR SEQ ID NO:7:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic
            DNA Linker"

( i i i ) HYPOTHETICAL: YES ( x i ) SEQUENCE DESCRIPTION: SEQ ID NO:7:

GTGCNNNNNN GCAC                                      14

( 2 ) INFORMATION FOR SEQ ID NO:8:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic
            DNA Linker"

( i i i ) HYPOTHETICAL: YES ( x i ) SEQUENCE DESCRIPTION: SEQ ID NO:8:

GCACNNNNNN GTGC                                      14

( 2 ) INFORMATION FOR SEQ ID NO:9:

( i ) SEQUENCE CHARACTERISTICS:
        ( A ) LENGTH: 10 base pairs ( B ) TYPE: nucleic acid
( C ) STRANDEDNESS: double
( D ) TOPOLOGY: linear ( i i ) MOLECULE TYPE: other nucleic acid
( A ) DESCRIPTION: /desc ="Synthetic DNA Linker"

( i i i ) HYPOTHETICAL: YES ( x i ) SEQUENCE DESCRIPTION: SEQ ID NO:9:

ACNNNNNNGT                                                                                      10

( 2 ) INFORMATION FOR SEQ ID NO:10:

( i ) SEQUENCE CHARACTERISTICS:
( A ) LENGTH: 14 base pairs
( B ) TYPE: nucleic acid
( C ) STRANDEDNESS: double
( D ) TOPOLOGY: linear ( i i ) MOLECULE TYPE: other nucleic acid
( A ) DESCRIPTION: /desc ="Synthetic DNA Linker"

( i i i ) HYPOTHETICAL: YES ( x i ) SEQUENCE DESCRIPTION: SEQ ID NO:10:

TAAGNNNNNN CTTA                                                                                 14

( 2 ) INFORMATION FOR SEQ ID NO:11:

( i ) SEQUENCE CHARACTERISTICS:
( A ) LENGTH: 14 base pairs
( B ) TYPE: nucleic acid
( C ) STRANDEDNESS: double
( D ) TOPOLOGY: linear ( i i ) MOLECULE TYPE: other nucleic acid
( A ) DESCRIPTION: /desc ="Synthetic DNA Linker"

( i i i ) HYPOTHETICAL: YES ( x i ) SEQUENCE DESCRIPTION: SEQ ID NO:11:

CGAGNNNNN CTCG                                                                                  14

( 2 ) INFORMATION FOR SEQ ID NO:12:

( i ) SEQUENCE CHARACTERISTICS:
( A ) LENGTH: 10 base pairs
( B ) TYPE: nucleic acid
( C ) STRANDEDNESS: double
( D ) TOPOLOGY: linear ( i i ) MOLECULE TYPE: other nucleic acid
( A ) DESCRIPTION: /desc ="Synthetic DNA Linker"

( i i i ) HYPOTHETICAL: YES ( x i ) SEQUENCE DESCRIPTION: SEQ ID NO:12:

AGNNNNNNCT                                                                                      10

( 2 ) INFORMATION FOR SEQ ID NO:13:

( i ) SEQUENCE CHARACTERISTICS:
( A ) LENGTH: 14 base pairs
( B ) TYPE: nucleic acid
( C ) STRANDEDNESS: double
( D ) TOPOLOGY: linear (i i) MOLECULE TYPE: other nucleic acid
(A) DESCRIPTION: /desc ="Synthetic DNA Linker"

(i i i) HYPOTHETICAL: YES (x i) SEQUENCE DESCRIPTION: SEQ ID NO:13:

GCAGNNNNNN CTGC 14

(2) INFORMATION FOR SEQ ID NO:14:

(i) SEQUENCE CHARACTERISTICS:
(A) LENGTH: 14 base pairs
(B) TYPE: nucleic acid
(C) STRANDEDNESS: double
(D) TOPOLOGY: linear (i i) MOLECULE TYPE: other nucleic acid
(A) DESCRIPTION: /desc ="Synthetic DNA Linker"

(i i i) HYPOTHETICAL: YES (x i) SEQUENCE DESCRIPTION: SEQ ID NO:14:

TAATNNNNNN ATTA 14

(2) INFORMATION FOR SEQ ID NO:15:

(i) SEQUENCE CHARACTERISTICS:
(A) LENGTH: 14 base pairs
(B) TYPE: nucleic acid
(C) STRANDEDNESS: double
(D) TOPOLOGY: linear (i i) MOLECULE TYPE: other nucleic acid
(A) DESCRIPTION: /desc ="Synthetic DNA Linker"

(i i i) HYPOTHETICAL: YES (x i) SEQUENCE DESCRIPTION: SEQ ID NO:15:

CGATNNNNNN ATCG 14

(2) INFORMATION FOR SEQ ID NO:16:

(i) SEQUENCE CHARACTERISTICS:
(A) LENGTH: 14 base pairs
(B) TYPE: nucleic acid
(C) STRANDEDNESS: double
(D) TOPOLOGY: linear (i i) MOLECULE TYPE: other nucleic acid
(A) DESCRIPTION: /desc ="Synthetic DNA Linker"

(i i i) HYPOTHETICAL: YES (x i) SEQUENCE DESCRIPTION: SEQ ID NO:16:

GCATNNNNNN ATGC 14

(2) INFORMATION FOR SEQ ID NO:17:

(i) SEQUENCE CHARACTERISTICS:
(A) LENGTH: 14 base pairs
(B) TYPE: nucleic acid
(C) STRANDEDNESS: double
(D) TOPOLOGY: linear (i i) MOLECULE TYPE: other nucleic acid
(A) DESCRIPTION: /desc ="Synthetic DNA Linker"

( i i i ) HYPOTHETICAL: YES ( x i ) SEQUENCE DESCRIPTION: SEQ ID NO:17:

ATCANNNNNN TGAT    14

( 2 ) INFORMATION FOR SEQ ID NO:18:

( i ) SEQUENCE CHARACTERISTICS:
    ( A ) LENGTH: 14 base pairs
    ( B ) TYPE: nucleic acid
    ( C ) STRANDEDNESS: double
    ( D ) TOPOLOGY: linear ( i i ) MOLECULE TYPE: other nucleic acid
    ( A ) DESCRIPTION: /desc ="Synthetic DNA Linker"

( i i i ) HYPOTHETICAL: YES ( x i ) SEQUENCE DESCRIPTION: SEQ ID NO:18:

TACANNNNNN TGTA    14

( 2 ) INFORMATION FOR SEQ ID NO:19:

( i ) SEQUENCE CHARACTERISTICS:
    ( A ) LENGTH: 14 base pairs
    ( B ) TYPE: nucleic acid
    ( C ) STRANDEDNESS: double
    ( D ) TOPOLOGY: linear ( i i ) MOLECULE TYPE: other nucleic acid
    ( A ) DESCRIPTION: /desc ="Synthetic DNA Linker"

( i i i ) HYPOTHETICAL: YES ( x i ) SEQUENCE DESCRIPTION: SEQ ID NO:19:

GCCANNNNNN TGGC    14

( 2 ) INFORMATION FOR SEQ ID NO:20:

( i ) SEQUENCE CHARACTERISTICS:
    ( A ) LENGTH: 14 base pairs
    ( B ) TYPE: nucleic acid
    ( C ) STRANDEDNESS: double
    ( D ) TOPOLOGY: linear ( i i ) MOLECULE TYPE: other nucleic acid
    ( A ) DESCRIPTION: /desc ="Synthetic DNA Linker"

( i i i ) HYPOTHETICAL: YES ( x i ) SEQUENCE DESCRIPTION: SEQ ID NO:20:

GCCCNNNNNN GGGC    14

( 2 ) INFORMATION FOR SEQ ID NO:21:

( i ) SEQUENCE CHARACTERISTICS:
    ( A ) LENGTH: 18 base pairs
    ( B ) TYPE: nucleic acid
    ( C ) STRANDEDNESS: double
    ( D ) TOPOLOGY: linear ( i i ) MOLECULE TYPE: other nucleic acid
    ( A ) DESCRIPTION: /desc ="Synthetic DNA Linker"

( i i i ) HYPOTHETICAL: YES ( x i ) SEQUENCE DESCRIPTION: SEQ ID NO:21:

CGCGCCNNNN NNGGCGCG                                                                18

(2) INFORMATION FOR SEQ ID NO:22:

(i) SEQUENCE CHARACTERISTICS:
        (A) LENGTH: 12 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc ="Synthetic DNA Linker"

(iii) HYPOTHETICAL: YES (xi) SEQUENCE DESCRIPTION: SEQ ID NO:22:

WCCNNNNNNG GW                                                                       12

(2) INFORMATION FOR SEQ ID NO:23:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc ="Synthetic DNA Linker"

(iii) HYPOTHETICAL: YES (xi) SEQUENCE DESCRIPTION: SEQ ID NO:23:

ATCCNNNNNN GGAT                                                                     14

(2) INFORMATION FOR SEQ ID NO:24:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc ="Synthetic DNA Linker"

(iii) HYPOTHETICAL: YES (xi) SEQUENCE DESCRIPTION: SEQ ID NO:24:

YUCCNNNNNN GGYU                                                                     14

(2) INFORMATION FOR SEQ ID NO:25:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc ="Synthetic DNA Linker"

(iii) HYPOTHETICAL: YES (xi) SEQUENCE DESCRIPTION: SEQ ID NO:25:

CGCCNNNNNN GGCG                                                                     14

(2) INFORMATION FOR SEQ ID NO:26:

( i ) SEQUENCE CHARACTERISTICS:
  ( A ) LENGTH: 16 base pairs
  ( B ) TYPE: nucleic acid
  ( C ) STRANDEDNESS: double
  ( D ) TOPOLOGY: linear ( i i ) MOLECULE TYPE: other nucleic acid
  ( A ) DESCRIPTION: /desc ="Synthetic DNA Linker"

( i i i ) HYPOTHETICAL: YES ( x i ) SEQUENCE DESCRIPTION: SEQ ID NO:26:

TNACCNNNNN NGGTNA                16

( 2 ) INFORMATION FOR SEQ ID NO:27:

( i ) SEQUENCE CHARACTERISTICS:
  ( A ) LENGTH: 16 base pairs
  ( B ) TYPE: nucleic acid
  ( C ) STRANDEDNESS: double
  ( D ) TOPOLOGY: linear ( i i ) MOLECULE TYPE: other nucleic acid
  ( A ) DESCRIPTION: /desc ="Synthetic DNA Linker"

( i i i ) HYPOTHETICAL: YES ( x i ) SEQUENCE DESCRIPTION: SEQ ID NO:27:

GNCC Y NNNNN NUGGNC              16

( 2 ) INFORMATION FOR SEQ ID NO:28:

( i ) SEQUENCE CHARACTERISTICS:
  ( A ) LENGTH: 14 base pairs
  ( B ) TYPE: nucleic acid
  ( C ) STRANDEDNESS: double
  ( D ) TOPOLOGY: linear ( i i ) MOLECULE TYPE: other nucleic acid
  ( A ) DESCRIPTION: /desc ="Synthetic DNA Linker"

( i i i ) HYPOTHETICAL: YES ( x i ) SEQUENCE DESCRIPTION: SEQ ID NO:28:

TACCNNNNNN GGTA                  14

( 2 ) INFORMATION FOR SEQ ID NO:29:

( i ) SEQUENCE CHARACTERISTICS:
  ( A ) LENGTH: 12 base pairs
  ( B ) TYPE: nucleic acid
  ( C ) STRANDEDNESS: double
  ( D ) TOPOLOGY: linear ( i i ) MOLECULE TYPE: other nucleic acid
  ( A ) DESCRIPTION: /desc ="Synthetic DNA Linker"

( i i i ) HYPOTHETICAL: YES ( x i ) SEQUENCE DESCRIPTION: SEQ ID NO:29:

NCCNNNNNNG GN                    12

( 2 ) INFORMATION FOR SEQ ID NO:30:

( i ) SEQUENCE CHARACTERISTICS:
  ( A ) LENGTH: 30 base pairs
  ( B ) TYPE: nucleic acid (C) STRANDEDNESS: double
(D) TOPOLOGY: linear (ii) MOLECULE TYPE: other nucleic acid
  (A) DESCRIPTION: /desc ="Synthetic DNA Linker"

(iii) HYPOTHETICAL: YES (xi) SEQUENCE DESCRIPTION: SEQ ID NO:30:

CCNNNNNGG CCNNNNNGG CCNNNNNGG                30

(2) INFORMATION FOR SEQ ID NO:31:

(i) SEQUENCE CHARACTERISTICS:
    (A) LENGTH: 14 base pairs
    (B) TYPE: nucleic acid
    (C) STRANDEDNESS: double
    (D) TOPOLOGY: linear (ii) MOLECULE TYPE: other nucleic acid
    (A) DESCRIPTION: /desc ="Synthetic DNA Linker"

(iii) HYPOTHETICAL: YES (xi) SEQUENCE DESCRIPTION: SEQ ID NO:31:

CGCGNNNNNN CGCG                              14

(2) INFORMATION FOR SEQ ID NO:32:

(i) SEQUENCE CHARACTERISTICS:
    (A) LENGTH: 14 base pairs
    (B) TYPE: nucleic acid
    (C) STRANDEDNESS: double
    (D) TOPOLOGY: linear (ii) MOLECULE TYPE: other nucleic acid
    (A) DESCRIPTION: /desc ="Synthetic DNA Linker"

(iii) HYPOTHETICAL: YES (xi) SEQUENCE DESCRIPTION: SEQ ID NO:32:

TACGNNNNNN CGTA                              14

(2) INFORMATION FOR SEQ ID NO:33:

(i) SEQUENCE CHARACTERISTICS:
    (A) LENGTH: 14 base pairs
    (B) TYPE: nucleic acid
    (C) STRANDEDNESS: double
    (D) TOPOLOGY: linear (ii) MOLECULE TYPE: other nucleic acid
    (A) DESCRIPTION: /desc ="Synthetic DNA Linker"

(iii) HYPOTHETICAL: YES (xi) SEQUENCE DESCRIPTION: SEQ ID NO:33:

GCCGNNNNNN CGGC                              14

(2) INFORMATION FOR SEQ ID NO:34:

(i) SEQUENCE CHARACTERISTICS:
    (A) LENGTH: 14 base pairs
    (B) TYPE: nucleic acid
    (C) STRANDEDNESS: double
    (D) TOPOLOGY: linear (ii) MOLECULE TYPE: other nucleic acid (A) DESCRIPTION: /desc ="Synthetic
                DNA Linker"

(iii) HYPOTHETICAL: YES (xi) SEQUENCE DESCRIPTION: SEQ ID NO:34:

ATCGNNNNNN CGAT                                                         14

(2) INFORMATION FOR SEQ ID NO:35:

(i) SEQUENCE CHARACTERISTICS:
            (A) LENGTH: 16 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc ="Synthetic
                DNA Linker"

(iii) HYPOTHETICAL: YES (xi) SEQUENCE DESCRIPTION: SEQ ID NO:35:

GWCCGNNNNN NCGGWC                                                       16

(2) INFORMATION FOR SEQ ID NO:36:

(i) SEQUENCE CHARACTERISTICS:
            (A) LENGTH: 18 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc ="Synthetic
                DNA Linker"

(iii) HYPOTHETICAL: YES (xi) SEQUENCE DESCRIPTION: SEQ ID NO:36:

CCGGCGNNNN NNCGCCGG                                                     18

(2) INFORMATION FOR SEQ ID NO:37:

(i) SEQUENCE CHARACTERISTICS:
            (A) LENGTH: 14 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc ="Synthetic
                DNA Linker"

(iii) HYPOTHETICAL: YES (xi) SEQUENCE DESCRIPTION: SEQ ID NO:37:

ATCTNNNNNN AGAT                                                         14

(2) INFORMATION FOR SEQ ID NO:38:

(i) SEQUENCE CHARACTERISTICS:
            (A) LENGTH: 16 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc ="Synthetic
                DNA Linker"

(iii) HYPOTHETICAL: YES ( x i ) SEQUENCE DESCRIPTION: SEQ ID NO:38:

GNCCTNNNNN NAGGNC    16

( 2 ) INFORMATION FOR SEQ ID NO:39:

( i ) SEQUENCE CHARACTERISTICS:
      ( A ) LENGTH: 14 base pairs
      ( B ) TYPE: nucleic acid
      ( C ) STRANDEDNESS: double
      ( D ) TOPOLOGY: linear ( i i ) MOLECULE TYPE: other nucleic acid
      ( A ) DESCRIPTION: /desc ="Synthetic
         DNA Linker"

( i i i ) HYPOTHETICAL: YES ( x i ) SEQUENCE DESCRIPTION: SEQ ID NO:39:

CGCTNNNNNN AGCG    14

( 2 ) INFORMATION FOR SEQ ID NO:40:

( i ) SEQUENCE CHARACTERISTICS:
      ( A ) LENGTH: 14 base pairs
      ( B ) TYPE: nucleic acid
      ( C ) STRANDEDNESS: double
      ( D ) TOPOLOGY: linear ( i i ) MOLECULE TYPE: other nucleic acid
      ( A ) DESCRIPTION: /desc ="Synthetic
         DNA Linker"

( i i i ) HYPOTHETICAL: YES ( x i ) SEQUENCE DESCRIPTION: SEQ ID NO:40:

CGGANNNNNN TCCG    14

( 2 ) INFORMATION FOR SEQ ID NO:41:

( i ) SEQUENCE CHARACTERISTICS:
      ( A ) LENGTH: 14 base pairs
      ( B ) TYPE: nucleic acid
      ( C ) STRANDEDNESS: double
      ( D ) TOPOLOGY: linear ( i i ) MOLECULE TYPE: other nucleic acid
      ( A ) DESCRIPTION: /desc ="Synthetic
         DNA Linker"

( i i i ) HYPOTHETICAL: YES ( x i ) SEQUENCE DESCRIPTION: SEQ ID NO:41:

ATGANNNNNN TCAT    14

( 2 ) INFORMATION FOR SEQ ID NO:42:

( i ) SEQUENCE CHARACTERISTICS:
      ( A ) LENGTH: 10 base pairs
      ( B ) TYPE: nucleic acid
      ( C ) STRANDEDNESS: double
      ( D ) TOPOLOGY: linear ( i i ) MOLECULE TYPE: other nucleic acid
      ( A ) DESCRIPTION: /desc ="Synthetic
         DNA Linker"

( i i i ) HYPOTHETICAL: YES ( x i ) SEQUENCE DESCRIPTION: SEQ ID NO:42:

GANNNNNNTC    10

( 2 ) INFORMATION FOR SEQ ID NO:43:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic
            DNA Linker"

( i i i ) HYPOTHETICAL: YES ( x i ) SEQUENCE DESCRIPTION: SEQ ID NO:43:

TAGANNNNN TCTA                                                  14

( 2 ) INFORMATION FOR SEQ ID NO:44:

( i ) SEQUENCE CHARACTERISTICS:
        ( A ) LENGTH: 24 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic
            DNA Linker"

( i i i ) HYPOTHETICAL: YES ( x i ) SEQUENCE DESCRIPTION: SEQ ID NO:44:

CNNNNNGGCN NNNNNGCCNN NNNG                        24

( 2 ) INFORMATION FOR SEQ ID NO:45:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic
            DNA Linker"

( i i i ) HYPOTHETICAL: YES ( x i ) SEQUENCE DESCRIPTION: SEQ ID NO:45:

TNAGCNNNN NGCTNA                                          16

( 2 ) INFORMATION FOR SEQ ID NO:46:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic
            DNA Linker"

( i i i ) HYPOTHETICAL: YES ( x i ) SEQUENCE DESCRIPTION: SEQ ID NO:46:

CGGCNNNNN GCCG                                                  14

( 2 ) INFORMATION FOR SEQ ID NO:47:

( i ) SEQUENCE CHARACTERISTICS:
  ( A ) LENGTH: 14 base pairs
  ( B ) TYPE: nucleic acid
  ( C ) STRANDEDNESS: double
  ( D ) TOPOLOGY: linear ( i i ) MOLECULE TYPE: other nucleic acid
  ( A ) DESCRIPTION: /desc ="Synthetic DNA Linker"

( i i i ) HYPOTHETICAL: YES ( x i ) SEQUENCE DESCRIPTION: SEQ ID NO:47:

GCGCNNNNNN GCGC　　　　　　　　　　　　　　14

( 2 ) INFORMATION FOR SEQ ID NO:48:

( i ) SEQUENCE CHARACTERISTICS:
  ( A ) LENGTH: 12 base pairs
  ( B ) TYPE: nucleic acid
  ( C ) STRANDEDNESS: double
  ( D ) TOPOLOGY: linear ( i i ) MOLECULE TYPE: other nucleic acid
  ( A ) DESCRIPTION: /desc ="Synthetic DNA Linker"

( i i i ) HYPOTHETICAL: YES ( x i ) SEQUENCE DESCRIPTION: SEQ ID NO:48:

NGCNNNNNNG CN　　　　　　　　　　　　　　12

( 2 ) INFORMATION FOR SEQ ID NO:49:

( i ) SEQUENCE CHARACTERISTICS:
  ( A ) LENGTH: 10 base pairs
  ( B ) TYPE: nucleic acid
  ( C ) STRANDEDNESS: double
  ( D ) TOPOLOGY: linear ( i i ) MOLECULE TYPE: other nucleic acid
  ( A ) DESCRIPTION: /desc ="Synthetic DNA Linker"

( i i i ) HYPOTHETICAL: YES ( x i ) SEQUENCE DESCRIPTION: SEQ ID NO:49:

GCNNNNNNGC　　　　　　　　　　　　　　　10

( 2 ) INFORMATION FOR SEQ ID NO:50:

( i ) SEQUENCE CHARACTERISTICS:
  ( A ) LENGTH: 24 base pairs
  ( B ) TYPE: nucleic acid
  ( C ) STRANDEDNESS: double
  ( D ) TOPOLOGY: linear ( i i ) MOLECULE TYPE: other nucleic acid
  ( A ) DESCRIPTION: /desc ="Synthetic DNA Linker"

( i i i ) HYPOTHETICAL: YES ( x i ) SEQUENCE DESCRIPTION: SEQ ID NO:50:

NNNNNNNGCN NNNNNGCNNN NNNN　　　　　　24

( 2 ) INFORMATION FOR SEQ ID NO:51:

( i ) SEQUENCE CHARACTERISTICS:
  ( A ) LENGTH: 14 base pairs
  ( B ) TYPE: nucleic acid
  ( C ) STRANDEDNESS: double (D) TOPOLOGY: linear (ii) MOLECULE TYPE: other nucleic acid
(A) DESCRIPTION: /desc ="Synthetic DNA Linker"

(iii) HYPOTHETICAL: YES (xi) SEQUENCE DESCRIPTION: SEQ ID NO:51:

TAGCNNNNNN GCTA 14

(2) INFORMATION FOR SEQ ID NO:52:

(i) SEQUENCE CHARACTERISTICS:
(A) LENGTH: 18 base pairs
(B) TYPE: nucleic acid
(C) STRANDEDNESS: double
(D) TOPOLOGY: linear (ii) MOLECULE TYPE: other nucleic acid
(A) DESCRIPTION: /desc ="Synthetic DNA Linker"

(iii) HYPOTHETICAL: YES (xi) SEQUENCE DESCRIPTION: SEQ ID NO:52:

GGCCGCNNNN NNGCGGCC 18

(2) INFORMATION FOR SEQ ID NO:53:

(i) SEQUENCE CHARACTERISTICS:
(A) LENGTH: 14 base pairs
(B) TYPE: nucleic acid
(C) STRANDEDNESS: double
(D) TOPOLOGY: linear (ii) MOLECULE TYPE: other nucleic acid
(A) DESCRIPTION: /desc ="Synthetic DNA Linker"

(iii) HYPOTHETICAL: YES (xi) SEQUENCE DESCRIPTION: SEQ ID NO:53:

ATGCNNNNNN GCAT 14

(2) INFORMATION FOR SEQ ID NO:54:

(i) SEQUENCE CHARACTERISTICS:
(A) LENGTH: 14 base pairs
(B) TYPE: nucleic acid
(C) STRANDEDNESS: double
(D) TOPOLOGY: linear (ii) MOLECULE TYPE: other nucleic acid
(A) DESCRIPTION: /desc ="Synthetic DNA Linker"

(iii) HYPOTHETICAL: YES (xi) SEQUENCE DESCRIPTION: SEQ ID NO:54:

CGGGNNNNNN CCCG 14

(2) INFORMATION FOR SEQ ID NO:55:

(i) SEQUENCE CHARACTERISTICS:
(A) LENGTH: 14 base pairs
(B) TYPE: nucleic acid
(C) STRANDEDNESS: double
(D) TOPOLOGY: linear (ii) MOLECULE TYPE: other nucleic acid
(A) DESCRIPTION: /desc ="Synthetic DNA Linker"

( i i i ) HYPOTHETICAL: YES ( x i ) SEQUENCE DESCRIPTION: SEQ ID NO:55:

TAGGNNNNNN CCTA 14

( 2 ) INFORMATION FOR SEQ ID NO:56:

( i ) SEQUENCE CHARACTERISTICS:
( A ) LENGTH: 24 base pairs
( B ) TYPE: nucleic acid
( C ) STRANDEDNESS: double
( D ) TOPOLOGY: linear ( i i ) MOLECULE TYPE: other nucleic acid
( A ) DESCRIPTION: /desc ="Synthetic DNA Linker"

( i i i ) HYPOTHETICAL: YES ( x i ) SEQUENCE DESCRIPTION: SEQ ID NO:56:

NNNNNNNGGN NNNNNCCNNN NNNN 24

( 2 ) INFORMATION FOR SEQ ID NO:57:

( i ) SEQUENCE CHARACTERISTICS:
( A ) LENGTH: 12 base pairs
( B ) TYPE: nucleic acid
( C ) STRANDEDNESS: double
( D ) TOPOLOGY: linear ( i i ) MOLECULE TYPE: other nucleic acid
( A ) DESCRIPTION: /desc ="Synthetic DNA Linker"

( i i i ) HYPOTHETICAL: YES ( x i ) SEQUENCE DESCRIPTION: SEQ ID NO:57:

WGGNNNNNNC CW 12

( 2 ) INFORMATION FOR SEQ ID NO:58:

( i ) SEQUENCE CHARACTERISTICS:
( A ) LENGTH: 26 base pairs
( B ) TYPE: nucleic acid
( C ) STRANDEDNESS: double
( D ) TOPOLOGY: linear ( i i ) MOLECULE TYPE: other nucleic acid
( A ) DESCRIPTION: /desc ="Synthetic DNA Linker"

( i i i ) HYPOTHETICAL: YES ( x i ) SEQUENCE DESCRIPTION: SEQ ID NO:58:

ANNNNNNTGG NNNNNNCCAN NNNNNT 26

( 2 ) INFORMATION FOR SEQ ID NO:59:

( i ) SEQUENCE CHARACTERISTICS:
( A ) LENGTH: 16 base pairs
( B ) TYPE: nucleic acid
( C ) STRANDEDNESS: double
( D ) TOPOLOGY: linear ( i i ) MOLECULE TYPE: other nucleic acid
( A ) DESCRIPTION: /desc ="Synthetic DNA Linker"

( i i i ) HYPOTHETICAL: YES ( x i ) SEQUENCE DESCRIPTION: SEQ ID NO:59:

TNAGGNNNNN NCCTNA                                        16

( 2 ) INFORMATION FOR SEQ ID NO:60:

( i ) SEQUENCE CHARACTERISTICS:
    ( A ) LENGTH: 24 base pairs
    ( B ) TYPE: nucleic acid
    ( C ) STRANDEDNESS: double
    ( D ) TOPOLOGY: linear ( i i ) MOLECULE TYPE: other nucleic acid
    ( A ) DESCRIPTION: /desc ="Synthetic
      DNA Linker"

( i i i ) HYPOTHETICAL: YES ( x i ) SEQUENCE DESCRIPTION: SEQ ID NO:60:

TNNNNNAGGN NNNNNCCTNN NNNA                               24

( 2 ) INFORMATION FOR SEQ ID NO:61:

( i ) SEQUENCE CHARACTERISTICS:
    ( A ) LENGTH: 10 base pairs
    ( B ) TYPE: nucleic acid
    ( C ) STRANDEDNESS: double
    ( D ) TOPOLOGY: linear ( i i ) MOLECULE TYPE: other nucleic acid
    ( A ) DESCRIPTION: /desc ="Synthetic
      DNA Linker"

( i i i ) HYPOTHETICAL: YES ( x i ) SEQUENCE DESCRIPTION: SEQ ID NO:61:

GGNNNNNNCC                                               10

( 2 ) INFORMATION FOR SEQ ID NO:62:

( i ) SEQUENCE CHARACTERISTICS:
    ( A ) LENGTH: 14 base pairs
    ( B ) TYPE: nucleic acid
    ( C ) STRANDEDNESS: double
    ( D ) TOPOLOGY: linear ( i i ) MOLECULE TYPE: other nucleic acid
    ( A ) DESCRIPTION: /desc ="Synthetic
      DNA Linker"

( i i i ) HYPOTHETICAL: YES ( x i ) SEQUENCE DESCRIPTION: SEQ ID NO:62:

GCGGNNNNNN CCGC                                          14

( 2 ) INFORMATION FOR SEQ ID NO:63:

( i ) SEQUENCE CHARACTERISTICS:
    ( A ) LENGTH: 12 base pairs
    ( B ) TYPE: nucleic acid
    ( C ) STRANDEDNESS: double
    ( D ) TOPOLOGY: linear ( i i ) MOLECULE TYPE: other nucleic acid
    ( A ) DESCRIPTION: /desc ="Synthetic
      DNA Linker"

( i i i ) HYPOTHETICAL: YES ( x i ) SEQUENCE DESCRIPTION: SEQ ID NO:63:

SGGNNNNNNC CS                                            12

( 2 ) INFORMATION FOR SEQ ID NO:64:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic
            DNA Linker"

( i i i ) HYPOTHETICAL: YES ( x i ) SEQUENCE DESCRIPTION: SEQ ID NO:64:

ATGGNNNNNN CCAT                                                          14

( 2 ) INFORMATION FOR SEQ ID NO:65:

( i ) SEQUENCE CHARACTERISTICS:
        ( A ) LENGTH: 24 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic
            DNA Linker"

( i i i ) HYPOTHETICAL: YES ( x i ) SEQUENCE DESCRIPTION: SEQ ID NO:65:

ANNNNNTGGN NNNNNCCANN NNNT                                 24

( 2 ) INFORMATION FOR SEQ ID NO:66:

( i ) SEQUENCE CHARACTERISTICS:
        ( A ) LENGTH: 32 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic
            DNA Linker"

( i i i ) HYPOTHETICAL: YES ( x i ) SEQUENCE DESCRIPTION: SEQ ID NO:66:

ANNNNNNNNN TGGNNNNNNC CANNNNNNNN NT                      32

( 2 ) INFORMATION FOR SEQ ID NO:67:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic
            DNA Linker"

( i i i ) HYPOTHETICAL: YES ( x i ) SEQUENCE DESCRIPTION: SEQ ID NO:67:

TGCAGGNNNN NNCCTGCA                                          18

( 2 ) INFORMATION FOR SEQ ID NO:68:

( i ) SEQUENCE CHARACTERISTICS:

( A ) LENGTH: 14 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic
            DNA Linker"

( i i i ) HYPOTHETICAL: YES ( x i ) SEQUENCE DESCRIPTION: SEQ ID NO:68:

U Y GTNNNNNN ACU Y                14

( 2 ) INFORMATION FOR SEQ ID NO:69:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic
            DNA Linker"

( i i i ) HYPOTHETICAL: YES ( x i ) SEQUENCE DESCRIPTION: SEQ ID NO:69:

CGGTNNNNNN ACCG                    14

( 2 ) INFORMATION FOR SEQ ID NO:70:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic
            DNA Linker"

( i i i ) HYPOTHETICAL: YES ( x i ) SEQUENCE DESCRIPTION: SEQ ID NO:70:

GCGTNNNNNN ACGC                    14

( 2 ) INFORMATION FOR SEQ ID NO:71:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic
            DNA Linker"

( i i i ) HYPOTHETICAL: YES ( x i ) SEQUENCE DESCRIPTION: SEQ ID NO:71:

TAGTNNNNNN ACTA                    14

( 2 ) INFORMATION FOR SEQ ID NO:72:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: linear (i i) MOLECULE TYPE: other nucleic acid
                (A) DESCRIPTION: /desc ="Synthetic
                        DNA Linker"

(i i i) HYPOTHETICAL: YES (x i) SEQUENCE DESCRIPTION: SEQ ID NO:72:

CGTCNNNNNN GACG                                              14

(2) INFORMATION FOR SEQ ID NO:73:

(i) SEQUENCE CHARACTERISTICS:
                (A) LENGTH: 14 base pairs
                (B) TYPE: nucleic acid
                (C) STRANDEDNESS: double
                (D) TOPOLOGY: linear (i i) MOLECULE TYPE: other nucleic acid
                (A) DESCRIPTION: /desc ="Synthetic
                        DNA Linker"

(i i i) HYPOTHETICAL: YES (x i) SEQUENCE DESCRIPTION: SEQ ID NO:73:

ATTCNNNNNN GAAT                                              14

(2) INFORMATION FOR SEQ ID NO:74:

(i) SEQUENCE CHARACTERISTICS:
                (A) LENGTH: 14 base pairs
                (B) TYPE: nucleic acid
                (C) STRANDEDNESS: double
                (D) TOPOLOGY: linear (i i) MOLECULE TYPE: other nucleic acid
                (A) DESCRIPTION: /desc ="Synthetic
                        DNA Linker"

(i i i) HYPOTHETICAL: YES (x i) SEQUENCE DESCRIPTION: SEQ ID NO:74:

GCTCNNNNNN GAGC                                              14

(2) INFORMATION FOR SEQ ID NO:75:

(i) SEQUENCE CHARACTERISTICS:
                (A) LENGTH: 10 base pairs
                (B) TYPE: nucleic acid
                (C) STRANDEDNESS: double
                (D) TOPOLOGY: linear (i i) MOLECULE TYPE: other nucleic acid
                (A) DESCRIPTION: /desc ="Synthetic
                        DNA Linker"

(i i i) HYPOTHETICAL: YES (x i) SEQUENCE DESCRIPTION: SEQ ID NO:75:

TCNNNNNNGA                                                   10

(2) INFORMATION FOR SEQ ID NO:76:

(i) SEQUENCE CHARACTERISTICS:
                (A) LENGTH: 26 base pairs
                (B) TYPE: nucleic acid
                (C) STRANDEDNESS: double
                (D) TOPOLOGY: linear (i i) MOLECULE TYPE: other nucleic acid
                (A) DESCRIPTION: /desc ="Synthetic
                        DNA Linker"

( i i i ) HYPOTHETICAL: YES ( x i ) SEQUENCE DESCRIPTION: SEQ ID NO:76:

CNNNNNNGTC NNNNNNGACN NNNNNG　　　　　　　　　　　　　26

( 2 ) INFORMATION FOR SEQ ID NO:77:

( i ) SEQUENCE CHARACTERISTICS:
        ( A ) LENGTH: 24 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic
            DNA Linker"

( i i i ) HYPOTHETICAL: YES ( x i ) SEQUENCE DESCRIPTION: SEQ ID NO:77:

CNNNNNGTCN NNNNNGACNN NNNG　　　　　　　　　　　　　24

( 2 ) INFORMATION FOR SEQ ID NO:78:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic
            DNA Linker"

( i i i ) HYPOTHETICAL: YES ( x i ) SEQUENCE DESCRIPTION: SEQ ID NO:78:

NTCNNNNNNG AN　　　　　　　　　　　　　　　　　　　　12

( 2 ) INFORMATION FOR SEQ ID NO:79:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic
            DNA Linker"

( i i i ) HYPOTHETICAL: YES ( x i ) SEQUENCE DESCRIPTION: SEQ ID NO:79:

CNNNGTCNNN NNNGACNNNG　　　　　　　　　　　　　　　20

( 2 ) INFORMATION FOR SEQ ID NO:80:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic
            DNA Linker"

( i i i ) HYPOTHETICAL: YES ( x i ) SEQUENCE DESCRIPTION: SEQ ID NO:80:

GNNNCTGNNN NNNCAGNNNC                                               20

( 2 ) INFORMATION FOR SEQ ID NO:81:

( i ) SEQUENCE CHARACTERISTICS:
                ( A ) LENGTH: 14 base pairs
                ( B ) TYPE: nucleic acid
                ( C ) STRANDEDNESS: double
                ( D ) TOPOLOGY: linear ( i i ) MOLECULE TYPE: other nucleic acid
                ( A ) DESCRIPTION: /desc ="Synthetic
                        DNA Linker"

( i i i ) HYPOTHETICAL: YES ( x i ) SEQUENCE DESCRIPTION: SEQ ID NO:81:

CGTGNNNNNN CACG                                                     14

( 2 ) INFORMATION FOR SEQ ID NO:82:

( i ) SEQUENCE CHARACTERISTICS:
                ( A ) LENGTH: 20 base pairs
                ( B ) TYPE: nucleic acid
                ( C ) STRANDEDNESS: double
                ( D ) TOPOLOGY: linear ( i i ) MOLECULE TYPE: other nucleic acid
                ( A ) DESCRIPTION: /desc ="Synthetic
                        DNA Linker"

( i i i ) HYPOTHETICAL: YES ( x i ) SEQUENCE DESCRIPTION: SEQ ID NO:82:

CNNNGTGNNN NNNCACNNNG                                               20

( 2 ) INFORMATION FOR SEQ ID NO:83:

( i ) SEQUENCE CHARACTERISTICS:
                ( A ) LENGTH: 14 base pairs
                ( B ) TYPE: nucleic acid
                ( C ) STRANDEDNESS: double
                ( D ) TOPOLOGY: linear ( i i ) MOLECULE TYPE: other nucleic acid
                ( A ) DESCRIPTION: /desc ="Synthetic
                        DNA Linker"

( i i i ) HYPOTHETICAL: YES ( x i ) SEQUENCE DESCRIPTION: SEQ ID NO:83:

ATTGNNNNNN CAAT                                                     14

( 2 ) INFORMATION FOR SEQ ID NO:84:

( i ) SEQUENCE CHARACTERISTICS:
                ( A ) LENGTH: 14 base pairs
                ( B ) TYPE: nucleic acid
                ( C ) STRANDEDNESS: double
                ( D ) TOPOLOGY: linear ( i i ) MOLECULE TYPE: other nucleic acid
                ( A ) DESCRIPTION: /desc ="Synthetic
                        DNA Linker"

( i i i ) HYPOTHETICAL: YES ( x i ) SEQUENCE DESCRIPTION: SEQ ID NO:84:

TATGNNNNNN CATA                                                     14

( 2 ) INFORMATION FOR SEQ ID NO:85:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic
            DNA Linker"

( i i i ) HYPOTHETICAL: YES ( x i ) SEQUENCE DESCRIPTION: SEQ ID NO:85:

TGNNNNNNCA                                            10

( 2 ) INFORMATION FOR SEQ ID NO:86:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic
            DNA Linker"

( i i i ) HYPOTHETICAL: YES ( x i ) SEQUENCE DESCRIPTION: SEQ ID NO:86:

CCGGTGNNNN NNCACCGG                          18

( 2 ) INFORMATION FOR SEQ ID NO:87:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic
            DNA Linker"

( i i i ) HYPOTHETICAL: YES ( x i ) SEQUENCE DESCRIPTION: SEQ ID NO:87:

ATTTNNNNNN AAAT                                14

( 2 ) INFORMATION FOR SEQ ID NO:88:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic
            DNA Linker"

( i i i ) HYPOTHETICAL: YES ( x i ) SEQUENCE DESCRIPTION: SEQ ID NO:88:

GCTTNNNNNN AAGC                                14

( 2 ) INFORMATION FOR SEQ ID NO:89:

( i ) SEQUENCE CHARACTERISTICS:
        ( A ) LENGTH: 10 base pairs (B) TYPE: nucleic acid
(C) STRANDEDNESS: double
(D) TOPOLOGY: linear (ii) MOLECULE TYPE: other nucleic acid
(A) DESCRIPTION: /desc ="Synthetic DNA Linker"

(iii) HYPOTHETICAL: YES (xi) SEQUENCE DESCRIPTION: SEQ ID NO:89:

TTNNNNNNAA        10

(2) INFORMATION FOR SEQ ID NO:90:

(i) SEQUENCE CHARACTERISTICS:
(A) LENGTH: 14 base pairs
(B) TYPE: nucleic acid
(C) STRANDEDNESS: double
(D) TOPOLOGY: linear (ii) MOLECULE TYPE: other nucleic acid
(A) DESCRIPTION: /desc ="Synthetic DNA Linker"

(iii) HYPOTHETICAL: YES (xi) SEQUENCE DESCRIPTION: SEQ ID NO:90:

GCTTGAATTC AAGC        14

(2) INFORMATION FOR SEQ ID NO:91:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: other nucleic acid
(A) DESCRIPTION: /desc ="hypothetical mRNA strand partially complementary to SEQ ID NO:92. See FIG. 1."

(iii) HYPOTHETICAL: YES (xi) SEQUENCE DESCRIPTION: SEQ ID NO:91:

CGUGCUGCUA AUGGCUGCAC GAAAAAAAAA        30

(2) INFORMATION FOR SEQ ID NO:92:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: /desc ="hypothetical cDNA first strand partially complementary to mRNA of SEQ ID NO:91. See FIG. 1."

(iii) HYPOTHETICAL: YES (xi) SEQUENCE DESCRIPTION: SEQ ID NO:92:

TTTGCAGCCA TTAGCAGCAC G        21

(2) INFORMATION FOR SEQ ID NO:93:

(i) SEQUENCE CHARACTERISTICS:
(A) LENGTH: 21 base pairs
(B) TYPE: nucleic acid
(C) STRANDEDNESS: double
(D) TOPOLOGY: linear ( i i ) MOLECULE TYPE: other nucleic acid
    ( A ) DESCRIPTION: /desc ="hypothetical cDNA. See
        FIG. 3."

( i i i ) HYPOTHETICAL: YES ( x i ) SEQUENCE DESCRIPTION: SEQ ID NO:93:

CGTGCTGCTA ATGGCTGCAA A                           21

( 2 ) INFORMATION FOR SEQ ID NO:94:

( i ) SEQUENCE CHARACTERISTICS:
        ( A ) LENGTH: 49 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="hypothetical cDNA of SEQ ID
            NO:93 ligated to terminal palindromic linkers. See
            FIG. 4."

( i i i ) HYPOTHETICAL: YES ( x i ) SEQUENCE DESCRIPTION: SEQ ID NO:94:

GCTTGAATTC AAGCCGTGCT GCTAATGGCT GCAAAGCTTG AATTCAAGC    49

( 2 ) INFORMATION FOR SEQ ID NO:95:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="hypothetical nucleic acid
            of SEQ ID NO:94 after cleavage with EcoRI and HindIII
            restriction endonucleases. Sequence is partially
            complementary to SEQ ID NO:96. See FIG. 5."

( i i i ) HYPOTHETICAL: YES ( x i ) SEQUENCE DESCRIPTION: SEQ ID NO:95:

AATTCAAGCC GTGCTGCTAA TGGCTGCAA                   29

( 2 ) INFORMATION FOR SEQ ID NO:96:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="hypothetical cDNA of SEQ ID
            NO:94 after cleavage with EcoRI and HindIII restriction
            endonucleases (strand 2). Sequence is partially
            complementary to SEQ ID NO:95. See FIG. 5."

( i i i ) HYPOTHETICAL: YES ( x i ) SEQUENCE DESCRIPTION: SEQ ID NO:96:

AGCTTTGCAG CCATTAGCAG CACGGCTTG                   29